United States Patent [19]
LeCocq et al.

[11] Patent Number: 5,573,502
[45] Date of Patent: Nov. 12, 1996

[54] DISPLAY PANEL AND CONTROLS FOR BLOOD MIXTURE DELIVERY SYSTEM

[75] Inventors: Andrew D. LeCocq, Hurst; Thomas C. Thompson; Kenneth A. Jones, both of McKinney; Martyn Abbott, Richardson; Albert M. Davis, Richardson; Andrew P. Mattson, Richardson, all of Tex.

[73] Assignee: Quest Medical, Inc., Dallas, Tex.

[21] Appl. No.: 204,532

[22] Filed: Mar. 1, 1994

Related U.S. Application Data

[63] Continuation-in-part of Ser. No. 67,683, May 26, 1993, Pat. No. 5,385,540.

[51] Int. Cl.$^6$ .................... A61M 37/00; A61M 31/00; A61M 1/00
[52] U.S. Cl. ................ 604/4; 604/65; 604/67; 604/113; 604/151; 128/DIG. 3
[58] Field of Search .................. 604/4–6, 113, 604/31, 53, 65, 151, 67; 128/637, 672, 695, DIG. 3, DIG. 13, DIG. 12, 660.04, 660.05

[56] References Cited

U.S. PATENT DOCUMENTS

| | | | |
|---|---|---|---|
| H1324 | 6/1994 | Dalke et al. | 128/DIG. 13 |
| T994,001 | 5/1980 | Buckberg et al. | 128/214 R |
| 4,236,880 | 12/1980 | Archibald | 417/478 |
| 4,401,431 | 8/1983 | Arp | 604/6 |
| 4,416,280 | 11/1983 | Carpenter et al. | 128/399 |
| 4,464,172 | 8/1984 | Lichtenstein | 604/65 |
| 4,466,804 | 8/1984 | Hino | 604/4 |
| 4,479,761 | 10/1984 | Bilstad et al. | |
| 4,568,330 | 2/1986 | Kujawski et al. | 604/53 |
| 4,657,490 | 4/1987 | Abbott | 417/478 |
| 4,696,671 | 9/1987 | Epstein et al. | 604/67 |
| 4,821,761 | 4/1989 | Aid et al. | 137/101.21 |
| 4,838,857 | 6/1989 | Strove et al. | 128/DIG. 12 |
| 4,874,359 | 10/1989 | White et al. | 604/4 |
| 4,883,455 | 11/1989 | Leonard | 604/4 |
| 5,171,212 | 12/1992 | Buck et al. | 604/4 |
| 5,322,500 | 6/1994 | Johnson et al. | 604/4 |

OTHER PUBLICATIONS

Eliot R. Rosenkrantz, M.D., et al., "Warm Induction of Cardioplegia with Glutamate–Enriched Blood in Coronary Patients with Cardiogenic Shock Who Are Dependent on Inotropic Drugs and Intra–Aortic Balloon Support," *The Journal of Thoracic and Cardiovascular Surgery* (1983) 86, pp. 507–518.

Philippe Menasche, M.D., et al., "Retrograde Coronary Sinus Perfusion: A Safe Alternative for Ensuring Cardioplegic Delivery in Aortic Valve Surgery," *The Annals of Thoracic Surgery*, vol. 34, No. 6 (Dec. 1982), pp. 647–658.

Eliot R. Rosenkranz, M.D., et al., "Myocardial Protection During Surgical Coronary Reperfusion," *The American College of Cardiology* (1983), pp. 1235–1246.

Eliot R. Rosenkranz, M.D., et al., "Benefits of Normothermic Induction of Blood Cardioplegia in Energy Depleted Hearts, with Maintenance of Arrest by Multidose Cold Blood Cardioplegic Infusions," *The Journal of Thoracic and Cardiovascular Surgery*, vol. 84, No. 5 (Nov., 1982), pp. 667–677.

(List continued on next page.)

*Primary Examiner*—John G. Weiss
*Assistant Examiner*—Dennis Ruhl
*Attorney, Agent, or Firm*—John W. Montgomery; Ross, Clapp, Korn & Montgomery, L.L.P.

[57] ABSTRACT

A display panel for use with a blood mixture fluid delivery system, which system has mechanisms for infusing blood mixture fluid to a patient and for controlling characteristics of the fluid delivery system. The display panel includes a visible schematic representation of a blood mixture fluid flow path through the fluid delivery system and visible displays of two or more of the controllable characteristics of the fluid delivery system, which visible displays are positioned along the schematic representation of the blood mixture fluid flow path.

61 Claims, 7 Drawing Sheets

OTHER PUBLICATIONS

John M. Robertson, M.D., et al., "Comparison of Distribution Beyond Coronary Stenoses of Blood and Asanguineous Cardioplegic Solutions," *The Journal of Thoracic and Cardiovascular Surgery*, vol. 1, No 1 (Jul. 1983), pp. 80–86.

David M. Follette, M.D., et al., "Advantages of Blood Cardioplegia Over Continuous Coronary Perfusion or Intermittent Ischemia," *The Journal of Thoracic and Cardiovascular Surgery*, vol. 76, No. 5 (Nov. 1978), pp. 604–619.

Arthur J. Roberts, et al., "Clinical Evaluation of the Relative Effectiveness of Multidose Crystalloid and Cold Blood Potassium Cardioplegia in Coronary Artery Bypass Graft Surgery; A Nonrandomized Matched–Pair Analysis," *The Annals of Thoracic Surgery*, vol. 33, No. 5 (May 1982), pp. 421–433.

Daniel Le Houerou, et al., "Minimal Hemodilution and Optimal Potassium Use During Normothermic Aerobic Arrest," *Annual Thoracic Surgery* (1992) 54:809–16, pp. 815–816.

Philippe Menasche, M.D., Ph. D., et al., "Simplified Method for Delivering Normothermic Blood Cardioplegia," *The Society of Thoracic Surgeons* (1993) 55:177–8.

Ad: "Cardioplegic Controller," Stöckert CAPS Cardioplegic Controller (Product Designation 27–60–00), Sorin Biomedical Inc. (two–page advertisement—©1993).

FIG. 5 (SET-UP MODE)
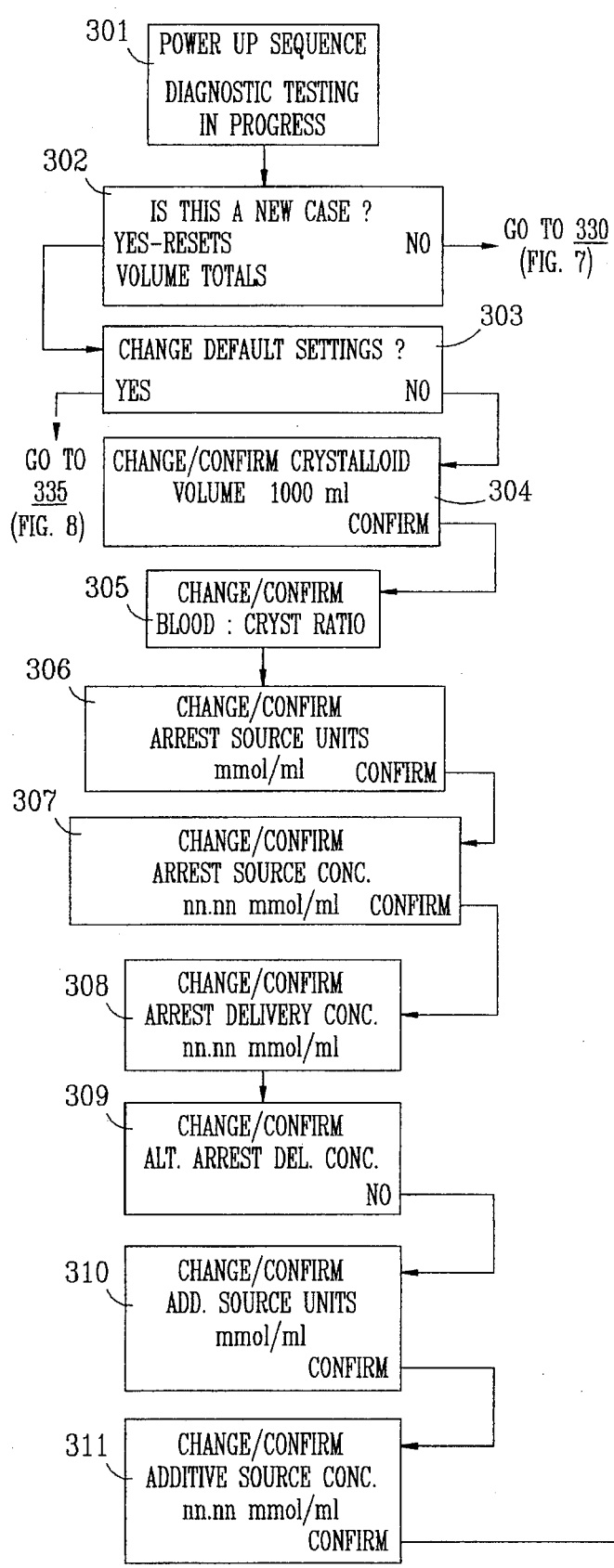
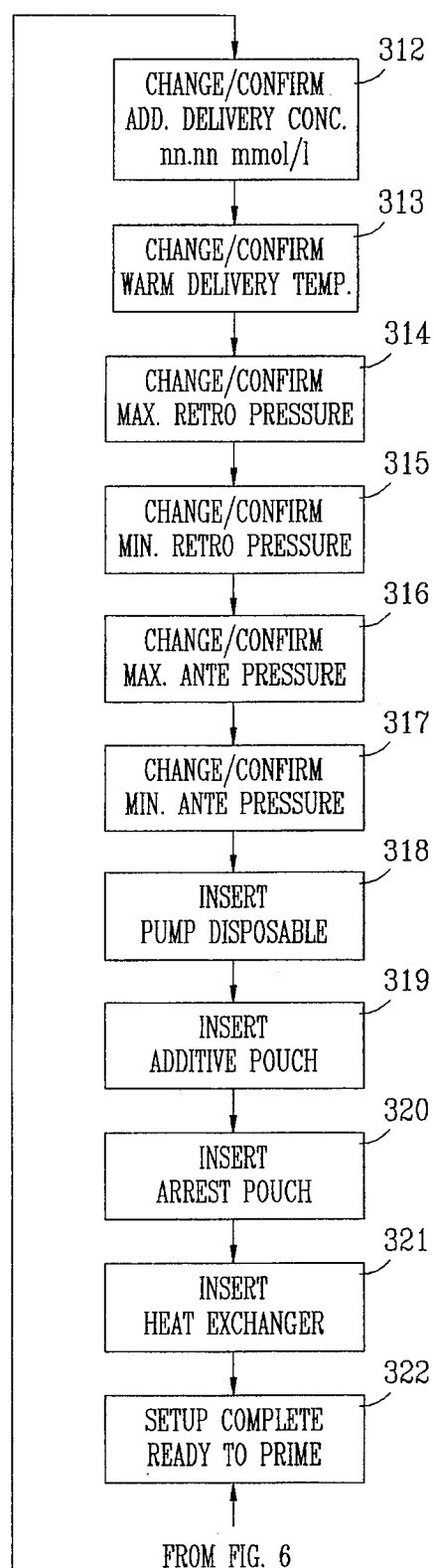

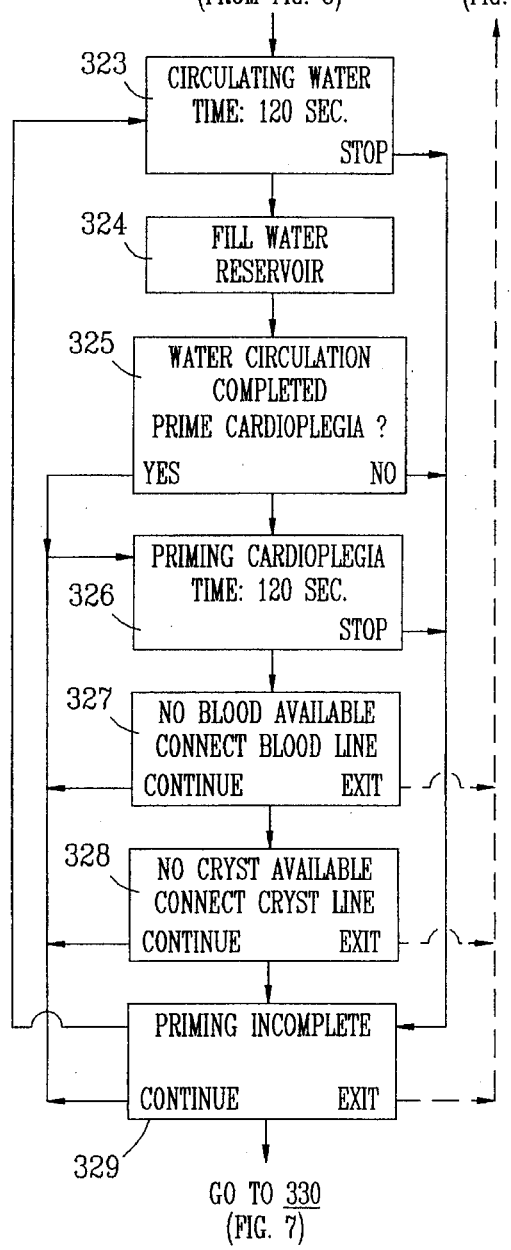
FIG. 6 (PRIME MODE)
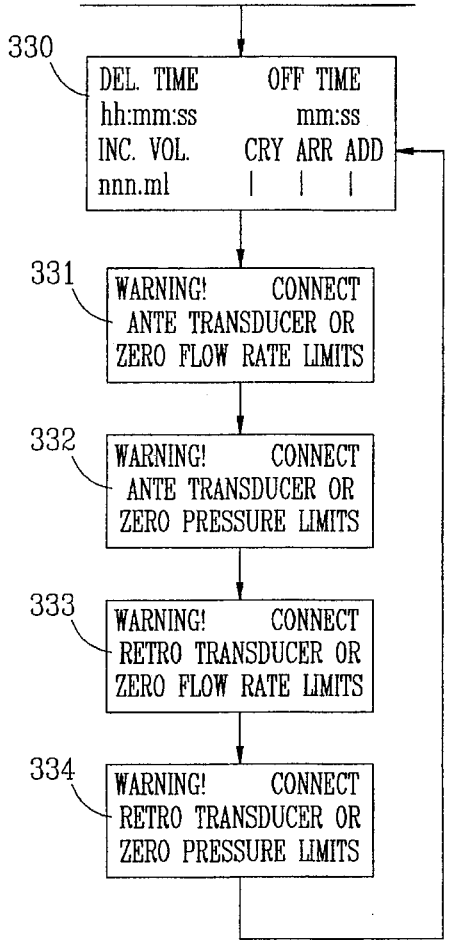
FIG. 7 (RUN MODE)
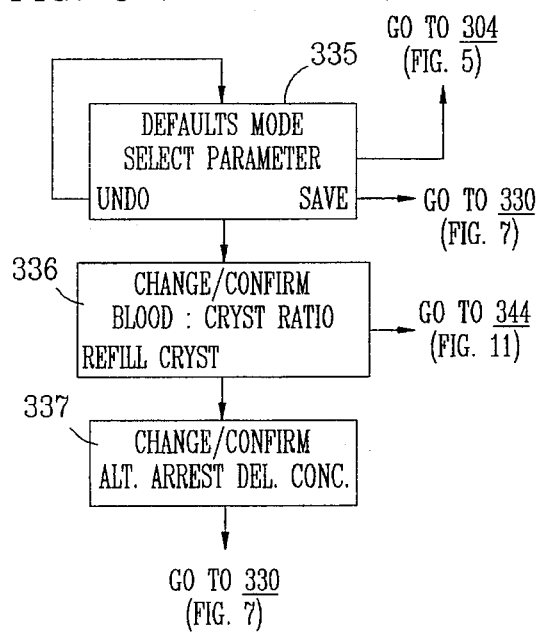
FIG. 8 (DEFAULTS MODE)

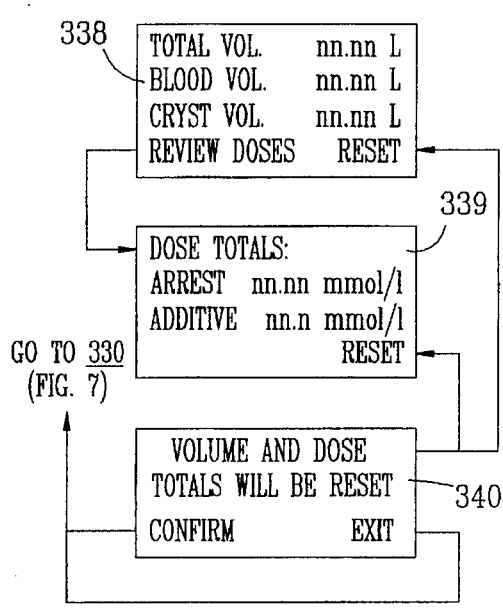
FIG. 9 (VOLUME MODE)
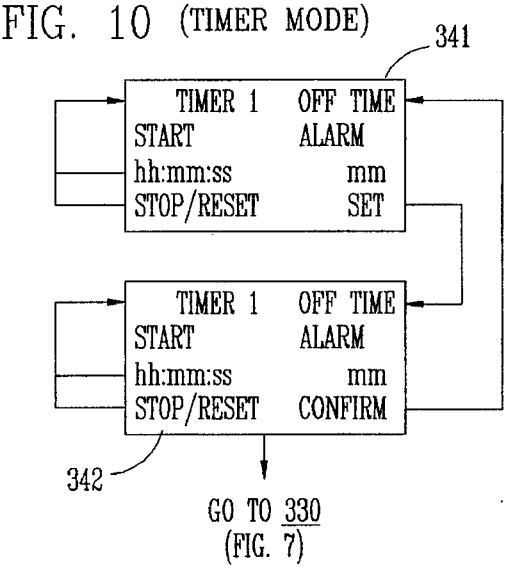
FIG. 10 (TIMER MODE)
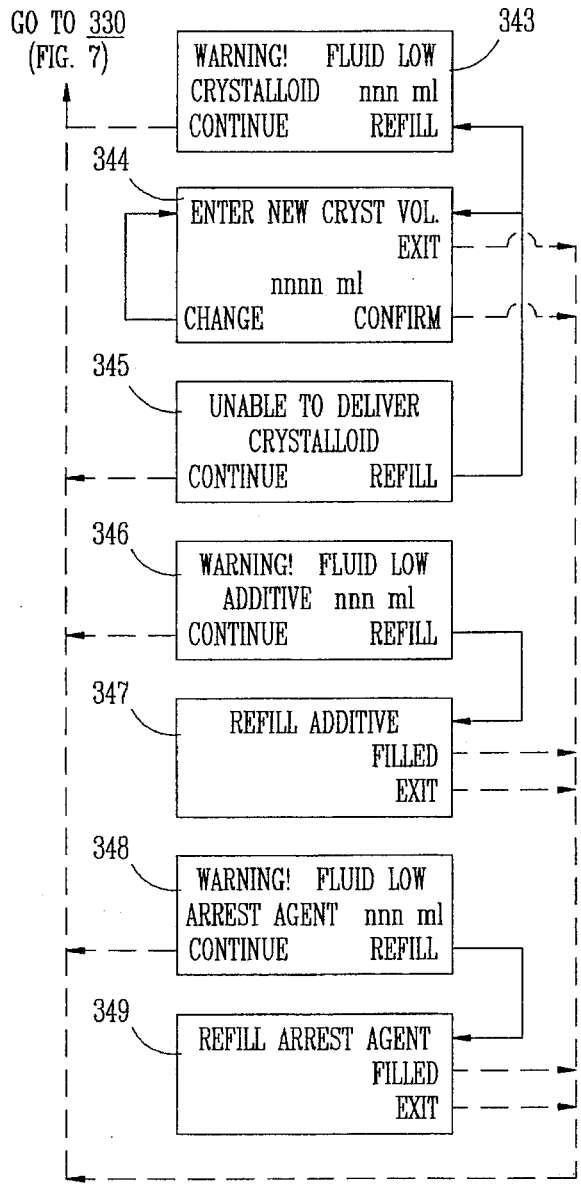
FIG. 11 (WARNING SCREENS)

DISPLAY PANEL AND CONTROLS FOR BLOOD MIXTURE DELIVERY SYSTEM

CROSS-REFERENCE TO RELATED APPLICATIONS

This application is a continuation-in-part of prior application Ser. No. 08/067,683 filed May 26, 1993 now U.S. Pat. No. 5,385,540 and is also related to co-owned, co-pending U.S. patent application entitled "Constant Pressure Blood Mixture Delivery System and Method" filed concurrently herewith, both of which related applications are incorporated by reference as if fully set forth herein.

TECHNICAL FIELD OF THE INVENTION

This invention relates to fluid delivery systems, and more particularly, the systems for blood mixture fluid delivery to an organ, limb or other body part of a patient during a medical procedure.

BACKGROUND OF THE INVENTION

In the performance of medical procedures, such as open heart surgery, isolated limb reperfusion, cerebral or neuro-perfusion, or the like, the patient may be supported by an extracorporeal blood circuit employing a heart/lung machine. Isolated organs or limbs may also be separately supplied with a blood mixture fluid, which may include a portion of the oxygenated blood from such an extracorporeal blood circuit, with or without other constituents. In the specific case of open heart surgery, for example, the heart is isolated from the vascular system, and venous blood is diverted into the extracorporeal blood circuit where it is oxygenated, temperature-controlled and returned to the patient's arterial side. A separate circuit is established for supplying a blood mixture fluid to the heart as the surgery proceeds. The constituents of such a blood mixture fluid will depend upon the procedure. In some situations, the blood mixture fluid will include whole blood; in other uses, it may be a mixture of blood, plasma and/or platelets or blood mixed with other constituents, agents and or additives. For example, during open heart surgery, a patient's heart may be supplied with a cardioplegia solution to stop the heart. A different blood fluid mixture might be used to maintain the heart during surgery, and another for reperfusion after surgery.

When the blood mixture fluid is a cardioplegia solution, it functions to still the heart, lower the metabolic requirements of the heart, protect the heart during periods of ischemia, and, finally, prepare the heart for reperfusion at the end of the procedure. Operation of the extracorporeal blood circuit as well as the cardioplegia delivery is performed by a trained perfusionist under the direction of the cardiovascular surgeon. The principal elements of advanced cardioplegia solutions are blood, representing a small fraction diverted from the output of the heart/lung machine, combined with a crystalloid solution. The crystalloid solution is a premixed aqueous saline or glucose solution, containing an arresting agent, such as potassium, to still the heart, metabolic substrates to feed the heart tissue, and may also contain buffers, special medications and additives to protect and preserve the heart during periods of ischemia and to prepare the heart for reperfusion with the normal blood supply. In addition, a minor but critical amount of potassium solution is added to the cardioplegic flow to still the heart.

Depending upon the requirements of the particular surgery, the cardioplegia solution may be cooled or warmed, and may be delivered in antegrade fashion to the aortic root or coronary ostia, or in a retrograde mode to the coronary sinus. The mode of delivery and composition of the cardioplegia solution may vary as the surgery proceeds, and are subject to the clinical judgment of the individual surgeon.

A typical cardioplegia delivery system employs two tubes routed through a single rotary peristaltic pump to forward both the separate blood and crystalloid solutions to a Y combining the two into a single flow. The ratio between the blood and crystalloid solution is determined simply by the relative diameters of the tubing carrying the two solutions, since each is mounted on the same rotary peristaltic mechanism and thus is forwarded by the same action. The tubing is usually provided in a 4:1 ratio of blood to crystalloid cross-sectional flow area, so that the rotary peristaltic pump is delivering blood and crystalloid to the delivery line in a ratio of approximately 4:1. Potassium is typically provided to the delivery line upstream of the pump from two alternate crystalloid solutions containing potassium, one having a relatively high concentration of potassium to stop the heart, the other a lower concentration of potassium sufficient to maintain the heart in the arrested state. The surgeon selects between the two sources as monitoring of the patient's condition indicates. The higher potassium concentration is utilized to arrest the heart, while the lower is used to maintain the stilled condition. The clinical team must provide sufficient potassium in the cardioplegia solution to establish the stilled condition of the heart and to maintain it during the procedure, while avoiding the risks associated with hyperkalemia and hemodilution which may result from excessive cardioplegia solution delivery.

Existing systems for delivery of cardioplegia are characterized by poor adaptability to varying requirements which the surgeon in charge may place upon the system as to parameters or characteristics of the cardioplegia fluid, including, for example, flow rate, pressure, ratios of blood to crystalloid, solution additives, temperature, and flow direction through the heart. For example, control of the ratio of blood to crystalloid solutions is not possible with present systems because the ratio is fixed by the size of the tubing routed through the peristaltic pump. Some of these parameters or characteristics have been controlled to a limited extent in prior systems. The control, if any, has been independently effectuated at separate instrumentation which has been interconnected with tubing to form a complete cardioplegia delivery system. The systems have particularly poor control over the cardioplegia delivery at low flow rates. Moreover, the shearing forces to which the blood in the cardioplegia line is subjected by peristaltic pump action risks damage to the blood. Furthermore, existing systems depend primarily on controlling the flow rate through manual adjustments in order to maintain a sufficient pressure to force the cardioplegia fluid through the vascular system of the heart while avoiding excessive pressure which might rupture the vessels or heart tissue. Also, the requirements are different for antegrade perfusion and for retrograde perfusion.

In our patent application filed on May 26, 1993, Ser. No. 08/067,683, now U.S. Pat. No. 5,385,540 which is incorporated herein by reference as if set forth herein, a cardioplegia system is provided for delivering cardioplegia solutions to a heart during open-heart surgery. The system cooperates with an extra-corporeal blood circuit employing a heart/lung machine. The system includes a conduit for diverting a portion of the blood flow from the heart/lung machine to the cardioplegia delivery line. A heat exchanger controls fluid temperature in the cardioplegia delivery line. A first pump combines blood from the conduit with a second fluid and delivers the combined fluid flow into the delivery line leading into the heat exchanger. A second pump is provided for delivery of a third fluid, typically the arrest agent, into the delivery line downstream from the first pump. The second pump has a flow rate less than about ten percent (10%) of the flow rate of the combined output of the first pump. Control means are included for adjusting the ratio of blood and second fluids which is delivered by the first pump and for adjusting the total volumetric rate of flow from the pump. Preferably, the volumetric flow rate of the first, second and third fluids are maintained at its desired percentage relative to each other. A third pump is provided for delivery of a fourth fluid, typically an additive, in combination with the output of the first and second pumps. Control means are provided for automatically controlling the output of the third pump in proportion to the variable output of the first pump.

In giving cardioplegia solutions for the heart, either for delivering an arrest agent which stops the heart for surgery or other additives which help take care of the heart, it is important to have adequate perfusion of all regions of the heart to ensure adequate preservation of the heart muscle. Delivery of an adequate flow rate does not guarantee that all regions of the heart are adequately perfused. In fact, most users increase the flow rate until an operating pressure is achieved and then attempt to operate at or near the same flow rate so that the pressure is likely to stay within a limited range. It is extremely difficult to control the flow rate in order to keep the pressure relatively constant because it is a continually dynamic system. Furthermore, it is not uncommon for the surgeon to pick up the heart or to move it and cause high resistance at the tip of the cannula, which increases the pressure in a dramatic fashion. If that is not immediately observed by the surgeon, the heart can be ruptured or other significant problems can arise.

One reason that the surgeon attempts to deliver the fluid at a pressure within a certain range is the fact that all of the flow directed towards the heart does not go through the blood vessels for nourishing the heart muscle tissues. For example, the veins which return the blood from the heart capillary beds to the coronary sinus form an intercommunicating network which when cardioplegia solution is delivered in the retrograde direction through the coronary sinus may route a percentage of the solution into veins which actually shunt the blood to the right atrium or into the left ventricle, bypassing the heart tissue. There may also be leakage around a balloon which is used to seal off the blood vessel, typically the coronary sinus, to which the fluid is being delivered. In the antegrade direction, occasionally the aortic valve may be defective or become incompetent due to manipulation of the heart by the surgeon. In either situation, the cardioplegia solution is delivered into the left ventricle rather than the coronary arteries. Therefore, as a result, one cannot be sure that upon delivering a certain amount of fluid, an adequate amount of the fluid will actually go through the tissues of the heart. Surgeons and their perfusionists use the fluid delivery pressure as a measure to indicate adequate delivery to the heart tissues. The particular flow rate necessary to achieve a desired pressure will depend upon the system leakage and the condition of the patient. The placement and seal of the delivery catheter into the aortic root or coronary ostia for antegrade infusion, or into the coronary sinus for retrograde infusion, along with the condition of the patient's blood vessels will also affect whether the flow provided actually moves through the heart tissue. Flow which leaks out of the system will not be useful for maintaining the healthy heart tissue and may contribute to hemodilution and hyperkalemia of the patient.

With prior blood mixture fluid delivery systems, the control of fluid delivery, as, for example, cardioplegia delivery, is based on the perfusionist's ability to observe changes in pressure and manually adjust the rate of delivery, accordingly. The true goal is to provide adequate flow through blood vessels supplying the tissues of the organ or limb. In the case of myocardial surgery, the goal is to have adequate flow to the heart at a pressure sufficient to ensure that the principal pathways are adequately perfused but not excessive as to avoid damage to the heart. Excessive pressures may result in rupture of blood vessels, such as the coronary sinus. Thus, safe and adequate delivery of blood mixture fluid to the intended tissue, such as delivery of cardioplegia solution through the heart, is dependent upon the pressure of delivery as well as the flow rate.

SUMMARY OF THE INVENTION

It is an object of the present invention to provide a display panel visually depicting a flow path for a blood mixture fluid delivery system with logical interconnection between two or more visual displays representing two or more controllable characteristics of the blood mixture fluid delivery system. Particularly, it is an object to provide the display panel depicting the flow path of a blood mixture fluid, a display of the blood mixture fluid flow rate and a display of the blood mixture pressure.

It is a further object of the invention to provide a display panel depicting a flow path for a blood mixture which is a cardioplegia solution and depicting a logical interconnection between two or more controllable characteristics of a cardioplegia fluid delivery system selected from visual displays of blood to crystalloid ratio, flow rate, amount of arrest agent, amount of an additive, temperature and delivery pressure of the cardioplegia solution.

It is a further object of the invention to provide a combined flow path display with a separate display panel for selectably displaying information in various modes, programmable target values for various controllable characteristics of the blood mixture fluid delivery system, programming information, system testing information, system warnings and operation instructions. In one particular embodiment, it is an object to provide a combined flow path display and separate selectable information display panel for a cardioplegia fluid delivery system.

It is another object of the invention to provide a display panel with a logical flow path in which one or more of the controllable characteristics of the system may be set using a single adjustable set knob activatable by depressible buttons associated with individual controllable characteristic displays.

It is a further object of the invention to provide visual displays of controllable characteristics of the system will be visually enhanced as with lighting or increased intensity display when that particular controllable characteristic is in a programmable or a set mode, It is a further object of the invention that priority and emphasis be provided for key or primary controllable characteristics, such as flow rate and pressure, through the use of display positions, display color variations or enlarged visual displays logically interconnected within the schematically depicted system flow path of the panel.

It is another object of the invention that visual displays of controllable characteristics of the system will be displayed with digital readouts corresponding to standard units of measure for the particular controllable characteristic, which is continuously updated according to the actual sensed value or the desired programmed value for a particular controllable characteristic.

Another object of the invention is to provide a display panel for a cardioplegia delivery system in which the direction of cardioplegia flow, whether antegrade or retrograde, is depicted depending upon the selected direction, and preferably to provide a dynamic display by which flow is schematically represented with pulsating or sequentially-activated indicator lights.

It is another object of the invention that an antegrade or retrograde selection valve be provided at the patient or on the instrument with appropriate selectable connections into a limb or an organ, such as the heart or the brain, and that control means be provided on the display panel for selecting pre-programmed antegrade or retrograde controllable characteristics based upon the position of the selection valve. Preferably, a feedback sensory input will be provided from the selector valve to the display panel for automatically determining the valve position so that antegrade or retrograde values and alarms are automatically selected. Further, preferably, a display panel will be provided with positioning controls for the antegrade/retrograde selector valve, which controls are operable from the display panel to simultaneously select and control the position of the valve, since the actuation to the desired position and invoke parameter values for the controllable characteristics which are desirable for antegrade or for retrograde flow as desired, selected and established.

It is another object of the invention to provide a display panel with both digital upper and lower limits for key controllable characteristics of the system and also, an analog display positioned between the upper and lower limits visually displaying the actual controllable characteristic value of the operating system in relationship to the upper and lower limits. Preferably, an analog display positioned between upper and lower flow limits will be provided. Also preferably, upper and lower pressure limits with an analog display of the actual pressure will be provided on the display panel.

It is a further object of the invention to provide a display panel from which a desired operating control mode may be selected for a cardioplegia delivery system. Preferably, the display panel provides controls for selecting among operating modes, including a set-up mode, a system priming mode, a system running mode, automatic delivery mode based on maintaining a desired pressure, a volume delivered and dose mode, a default parameter setting mode and a timer mode.

It is a further object to provide an information screen adjacent to the flow path representation of the control panel. The information screen is operatively connected to provide useful or helpful information to the user according to the mode of operation, the system parameters, and the condition of the system. Further, preferably function keys and variable function keys are provided on the display panel adjacent to the information screen for receiving operator input responsive to preprogrammed inquiries displayed on the information screen.

It is also an object of the invention to provide controls for operating the blood mixture fluid delivery system at a constant fluid delivery pressure to a patient. Preferably, the constant pressure controls include means for initially adjusting flow rate to obtain a desired delivery pressure and subsequently switching to an automatic constant pressure mode at which the flow rate is automatically adjusted to maintain the desired delivery pressure.

It is a further object of the invention to provide an operator control panel by which an observable volumetric flow rate can be adjustably controlled while observing a resulting patient delivery pressure on the same display panel. Preferably, upper and lower pressure limits are established through said control panel either set by the operator or automatically set to preprogrammed controls whether default limits or automatically calculated and set based upon a preprogrammed algorithm and the existing delivery pressure. Further preferably, it is an object to have an automatic constant pressure mode which can be selectively activated by the operator from the control panel upon obtaining a desired pressure using the adjusted flow rate and the resulting observed patient delivery pressure. When in the constant pressure mode, alarms are provided to inform the perfusionist when the instrument would have to adjust flow rate below or above preset high and low flow rate limits.

BRIEF DESCRIPTION OF THE DRAWINGS

These and other object, features and advantages of the invention will become more evident with reference to the drawings in which like reference numerals represent like elements and in which:

FIG. 5 schematically depicts a flow chart for display panel operation in a set-up mode;

FIG. 6 schematically depicts a flow diagram for the display panel controls in a system priming mode;

FIG. 7 is a schematic flow diagram of the display panel controls in the system run mode;

FIG. 8 is a schematic flow diagram of the operation and display panel and controls in the default mode;

FIG. 9 is a schematic flow diagram of information screen messages of the display panel controls operating in a volume and dose total mode;

FIG. 10 is a schematic flow diagram of information screen messages of the display panel controls operating in a timer mode according to the present invention; and FIG. 11 is a schematic flow diagram of information screen messages of the display panel controls operating in any of the various modes showing warning messages.

DETAILED DESCRIPTION OF THE PREFERRED EMBODIMENTS

Figure 1:
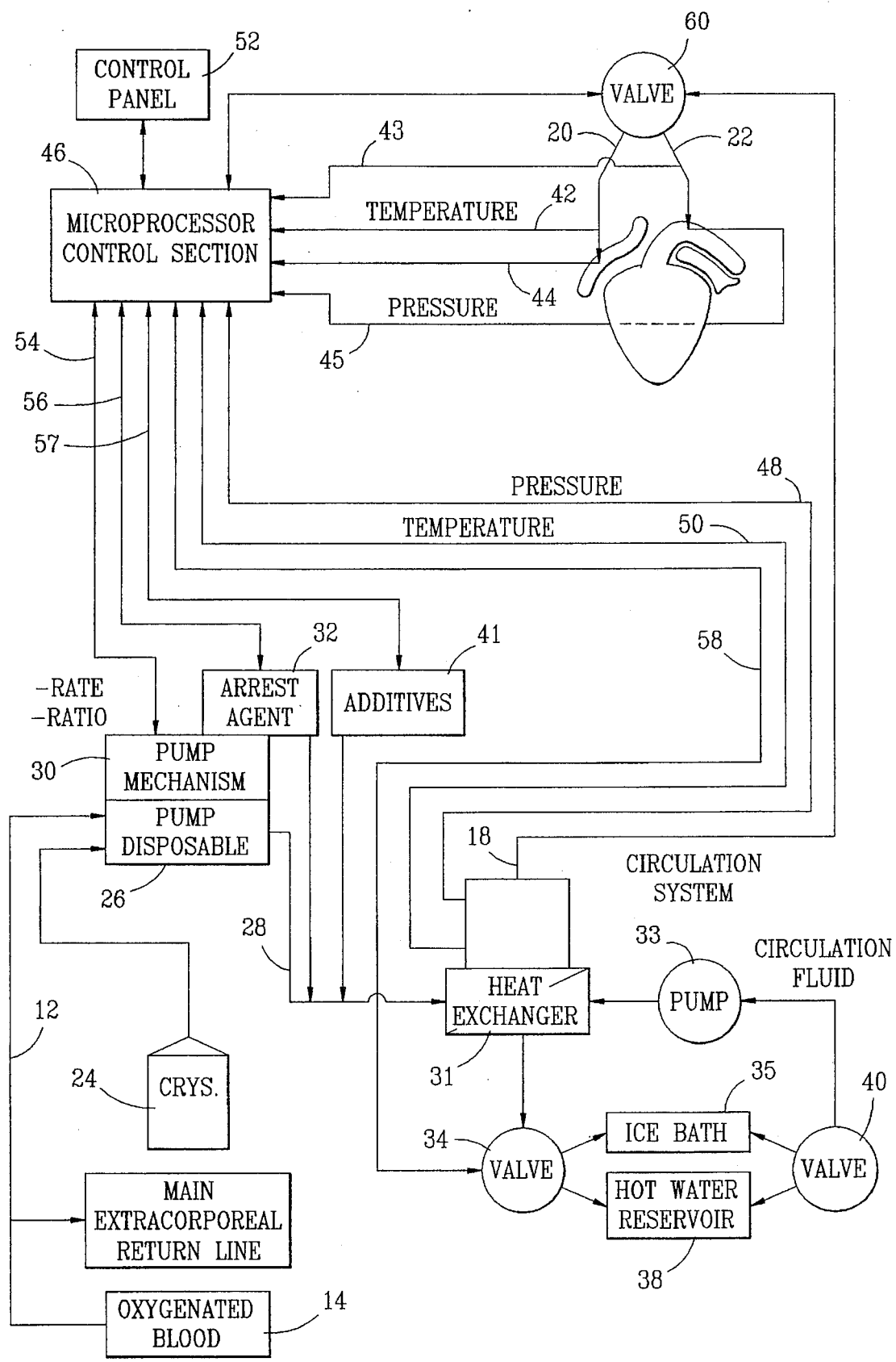
FIG. 1 is a schematic layout of a preferred embodiment of a cardioplegia delivery system for which a display panel according to the invention is useful.

FIG. 1 depicts one embodiment of a blood mixture fluid delivery system 10, which for purposes of example this application will be a cardioplegia delivery system 10. It will be understood that many of the same advantages of the various inventive aspects will also be obtained with blood mixture fluid delivery systems for other medical procedures. For example, isolated limb perfusion, cerebral or neuroperfusion, or other organ surgery or perfusion for which delivery of a blood mixture fluid will be beneficial. The term "blood mixture fluid", as used herein, shall mean a fluid which consists, in whole or in part, of blood or constituents of blood, such as blood cells, platelets or plasma, which may or may not be mixed with other non-blood constituents according to a particular medical procedure or protocol.

As depicted in FIG. 1, a cardioplegia delivery system 10 is established to provide solution to the heart of a patient during open heart surgery. The principal component of the cardioplegic solution is blood delivered to the system through conduit 12 which is connected to the output of the oxygenator 14 of the heart/lung machine sustaining the patient's vascular system while the heart is isolated therefrom during surgery. Oxygenator 14 provides arterial blood in the main extracorporeal circuit through a return line 16 to the patient's aorta. A fraction, usually about 10%, of the heart/lung machine output is diverted into conduit 12 for processing by the cardioplegic circuit and forwarding to the patient's heart through cardioplegia delivery line 18. The cardioplegic solution flowing through line 18 may be delivered through antegrade line 20 to the aortic root, or through retrograde line 22 to the coronary sinus.

A crystalloid solution is stored in container 24 for combination with blood flowing in line 12 in a disposable pumping cassette 26. The output of cassette 26 is supplied through line 28 to a heat exchanger 31. Pump cassette 26 is controlled by an electromechanical pump mechanism 30 in which cassette 26 is mounted. A second pump 32 containing a heart arresting agent such as a potassium solution supplies its output to line 28 downstream from the pump cassette 26. A third pump 41 may also be included to supply any variety of additives as may be desirable for a particular operation or as may be otherwise requested by the surgeon or by the operating team. The output will be injected into line 28 downstream from cassette 26.

Preferably, pumps 32 and 41 may be syringe pumps or volumetric pouches of a type well known in the infusion art. In the case where pump 32 is a syringe pump, a solution containing a heart arresting agent such as potassium may be loaded into a syringe, and the syringe mounted in pump 32 which progressively depresses the syringe plunger to deliver potassium solution to line 28. The flow rates of potassium solution are less than about 10%, and preferably less than about 5%, of the total flow rate issuing from pump cassette 26. An accurately controllable pump, such as a syringe pump, may be advantageously used in applications where a particular fluid additive or constituent must be an accurately controlled small portion, less than about 10%, of the total flow volume. Similarly, other additives will typically be limited to a small percentage so that accurate control on pump 41 is advantageous.

In the heat exchanger 31, the cardioplegic solution is juxtaposed with a circulating temperature controlled fluid to adjust the temperature of the solution prior to forwarding the solution to the heart through line 18. Preferably pump 33 circulates temperature controlled fluid through the heat exchanger 31 either by push or pull. FIG. 1 depicts a push through coolant system in which a pump 33 circulates the control fluid through heat exchanger 31 and then to a two-way valve 34, which valve 34 may direct the circulating fluid either to an ice bath 36 for cooling or a heated water reservoir 38 for heating. The circulating fluid is then pumped via valve 40 back through the heat exchanger 31 where the cardioplegia solution receives heating or cooling without contamination across a sealed heat transfer material or membrane within the heat exchanger 31.

The system includes patient monitoring of myocardial temperature along the signal path 42 and heart aortic root pressure along signal path 45 or coronary sinus pressure along signal path 44 communicating to a central microprocessor control section 46. In addition, the pressure and temperature of the cardioplegic solution in delivery line 18 is sensed and the data is forwarded along signal paths 48 and 50 to the control microprocessor 46. Data input to microprocessor 46 through control panel 52 may include an advantageous combination of the following parameters:

1. Desired overall volumetric flow rate through disposable pump cassette 26.
2. Desired and measured pressure of the cardioplegia fluid delivered to the patient.
3. Desired blood/crystalloid ratio to be forwarded by disposable pump cassette 26.
4. Desired potassium concentration to be established by pump 32.
5. Desired and measured temperature of solution in cardioplegia delivery line 18.
6. Safety parameters such as the pressure of the cardioplegia solution in the system or upper and lower limits for pressure in the patient.

In response to the data input through the control panel 52 and the monitored conditions along signal paths 42, 43, 44, 45, 48 and 50, microprocessor control section 46 controls the operation of pump mechanism 30 via signal path 54, and of potassium syringe pump 32 by signal along path 56. The control signals for a third pump 41 for additives may be communicated along path 57 between the control section 46 and pump 41. In addition, microprocessor control section 46 controls the circulation of fluid in the heat exchanger circulation path along signal path 58 either for obtaining a desired patient temperature or a desired output solution temperature. Further, the safety parameters such as pressure limits for a particular procedure or a particular patient may be controlled based upon input settings or based upon preset standards, as for example, one range of acceptable pressure limits for antegrade and another range for retrograde cardioplegia. The ranges may be set by the operator or may be set automatically based upon preprogrammed default values or may be calculated based upon preprogrammed algorithms in relation to a selected desired patient delivery pressure.

Communication connections or signal pathways 42, 43, 44, 45, 48, 50, 54, 57, 58 and any others as may be appropriate can be electrical signals through conducting wires, light signals through optical fibers or transmitter radio, ultrasonic or light signals.

In accordance with the invention, the microprocessor controller section 46 controls the pump mechanism 30 to combine crystalloid from container 24 and blood from line 12 in any selected ratio over a broad range of blood/crystalloid ratios. The controller 46 may command the pump mechanism 30 to deliver blood without crystalloid addition. A preferred range for the blood/crystalloid ratio adjustment capability is from 0 to 20:1 or all blood. The rate of flow produced by the pump mechanism 30 of the combined output from disposable pump cassette 26 is preferably variable from 0 to 500 milliliters per minute. The pump mechanism 30 may be operated by microprocessor 46 in either a continuous or intermittent mode by instruction through control panel 52. The arrest agent syringe pump 32 is automatically controlled to deliver at a rate such that the introduction of an arrest agent, such as a potassium solution, to line 28 is automatically maintained at the selected concentration vis-a-vis the flow of disposable cassette 26, without regard to changes requested in the flow rate from pump cassette 26 or changes in the blood/crystalloid ratio, requested of the pump mechanism 30 through microprocessor 46. Flow rates may be requested directly from a control panel by the operator.

Figure 2:
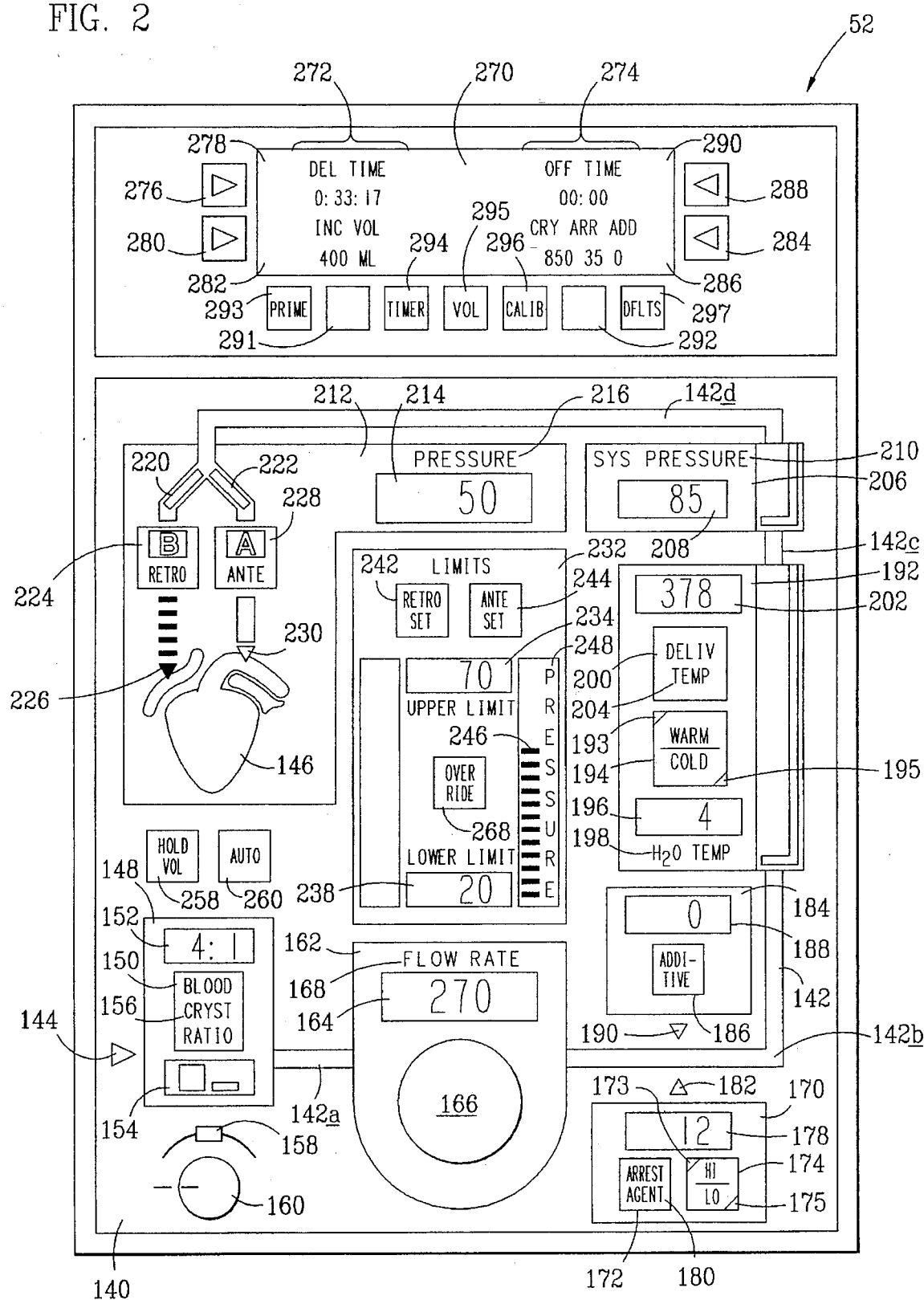
FIG. 2 is a front elevation view of a preferred embodiment of a display panel according to the present invention.

FIG. 2 is a detailed perspective view of a preferred embodiment of display panel 52. Display panel 52 has a front face 140 which is viewable from a wide frontal angular area, including substantially 180°. In the preferred embodiment, a substantially flat face 140 works well and is constructable using standard molding techniques, stamping techniques and components. Advantageously, a flow path 142 is visually depicted on the front panel interconnecting with portions of the substantially visually continuous flow path interconnecting two or more system component display areas, as with interconnecting portions 142a, 142b, 142c and 142d. Preferably, the two or more system components are those which are those system components which represent characteristic elements of the system which are adjustable through controls operably interconnected with the control panel 52, such as through a microprocessor control section 46 (as shown schematically in FIG. 1.) Also preferably, the visual depiction of the flow path 142 is formed with sufficient width and having sufficient contrasting color between the flow path 142 and the face 140, as for example, with a red flow path line 142 on a white or light beige or light grey background base 140. A width of approximately 3/16 of an inch to 5/16 of an inch (about 0.5 cm to 0.8 cm) with a bright oxygenated blood red color on a light grey background has been found to be easily visually perceptible from normal viewing distances in an operating room. It being observed that the normal maximum distance which the perfusionist is likely to move from a control panel during an operation will be about 9 to 15 feet (about 3–5 meters).

Prior control mechanisms for cardioplegia fluid delivery typically have various separate and independently located controls and visually independent displays separately connected with the various independent controls. Thus, the present control panel 52 advantageously incorporates at least two system component displays on the same display panels, which system components are located along a visually perceptible flow path 142, preferably in a logical sequence, which is characteristic of a cardioplegia perfusion system. While the invention will be described in connection with a preferred embodiment in which display areas for all the major controllable characteristics or parameters of a cardioplegia system, all located in a logical sequence, it will be understood by those skilled in the art that many of the advantages of the inventive display can be obtained through placing displays of at least two or more controllable parameters of a blood mixture mixture fluid delivery system on a single display panel arranged and interconnected in a logical sequence along a flow path. By way of example, and also because of the many specific advantages of the invention for open heart surgery, the invention will be described below in connection with a cardioplegia delivery system 10.

In the preferred embodiment, the flow path is provided with a start indicator 142, such as an arrow or arrowhead 144, which may be illuminated when the system is in an "on" position. Also, the flow path 142 is provided with a depiction of the delivery and of the flow path, as with a depiction of an organ, limb or other part of a patent, such as a heart 146, at the opposite end of the flow path from the start 144.

One of the first components which has desirably adjustable characteristics for the perfusionist is a blood-to-crystalloid ratio display area 148 and the display area 148 includes an adjustment actuation button 150, a digital display 152, a dynamic pump action display 154, and a label 156 associated with the digital display 152 and the dynamic pump action display 154 so that the operator will immediately understand which component of the system is represented by those displays within area 148. Whenever the pump is operating, display 154 is animated to show up and down pump action so that the operator immediately recognizes whether the system is operating. Upon depressing adjustment button 156, the set mode is actuated for establishing a desired blood-to-crystalloid ratio. Preferably, button 150 becomes lighted to indicate it is in an adjustment mode or a "set-up" mode and the digits within digital display 152 become brighter so that the operator is immediately notified that the blood-to-crystalloid ratio is in a condition for being set. Also, a set indicator light 158 display comes on or is otherwise lighted and the adjustment knob 160 is activated for manually adjusting the desired blood-to-crystalloid ratio, which adjustments will be continuously displayed within digital display 152. Once the desired ratio is established, then the operator again toggles the button 150 so that it is in an out position, turning off the light therebehind, dimming the digital display 152 and disconnecting knob 160 so that the set light 158 goes off.

The operation of the adjustment knob 160 in connection with setting various ones of the adjustable parameters of the system will be explained more fully below with respect to FIGS. 4–7. For a preliminary understanding of the preferred embodiment, the set knob 160 is engageable with the adjustment actuation switches or buttons which are associated with various ones of the display areas for components of the system which may be periodically adjusted. These components do not necessarily require adjustment for each patient so that a single adjustment knob 160 can be used with separate components while the others are maintained at a previous setting.

Flow rate display area 162 includes a digital display area 164 and a continuously engaged flow rate adjustment knob 166. The flow rate display area 162 also includes a label 168 adjacent to the digital display 164 so that the operator, perfusionist or surgeon immediately associates the digital display with the appropriate adjustable characteristic or parameter of the system. As the flow rate is typically the primary variable feature with respect to each patient, the adjustment knob 166 is continuously engaged and does not require actuation of an adjustment switch in order to engage the adjustment knob. The perfusionist may variably dial in the flow rate as required for each patient. It will be seen in the embodiment depicted in FIG. 2, flow rate area 162 follows closely adjacent to the blood-to-crystalloid ratio display area 148 along flow path 142 as it is a logical sequence corresponding to the system depicted in FIG. 1, in which the blood and crystalloid is pumped to the patient. The flow rate controls the rate of pumping. Its position on the display through a visual and logical correlation to the system which is understandable by the perfusionist and which reduces confusion and facilitates quick reaction by the perfusionist to any changing conditions during surgery. Normally, the perfusionist gradually increases the flow rate from a low initial value up to a defined pressure value, while watching an indicator of the pressure of the cardioplegia fluid at a catheter interconnected with the heart. The defined pressure will depend upon overall considerations, including whether the system is being operated in a retrograde flow or an antegrade flow direction. The perfusionist typically approaches the defined pressure slowly so that damage to the blood vessels supplying the heart with cardioplegia fluid is avoided.

As used in this application, the term "defined", when used to describe a particular value or a particular controllable characteristic, such as a "defined flow rate," a "defined pressure," a "defined concentration," a "defined temperature" or other defined characteristic or value, will have a meaning which includes any established value or characteristic, including a value or a characteristic as desired by perfusionists or surgeons, or a value or characteristic which is set by the perfusionist or doctor at the time of surgery, or a value or characteristic which is predetermined by the perfusionist, doctor or which is predetermined by established protocol for a particular procedure, or a preset value, or a value which is calculated by the microprocessor control according to preprogrammed algorithms, or a value which may be existing in the microprocessor memory, such as a default value or such as the last value set during a previous procedure using the same machine.

In normal cardioplegia delivery, as depicted in the system indicated in FIG. 1, an arrest agent will be added to the cardioplegia fluid at one high level of concentration initially in order to stop the heart from beating and subsequently after the heart has been sufficiently stopped from beating, will be maintained in an arrested condition with a low concentration of the arresting agent in the cardioplegia solution. Correspondingly, on the control panel 52 of FIG. 2, the arrest agent display area 170 preferably includes an arrest agent adjustment switch 172 which may be a depressible two position switch and also a high or low concentration selection switch 174, both of which are activatable to engage adjustment or set knob 160 and cause the set light 158 to light up. The digits in digital display 178 will also become brightened when the adjustment switch 172 is activated. When the value of the arrest agent concentration displayed in digital display 178 is greater than zero, then an on indicator light 182 will become activated. Preferably, the on light is in the shape of an arrow or arrowhead, which visually conveys the concept that an arrest agent will be entering the flow path 142 which will be carried to the heart 146 of the patient. Uniquely, the high concentration or high amount of arrest agent (i.e., the amount or mixture which will stop an initially beating heart) can be adjusted separately from the adjustment of a low concentration merely by pressing or toggling the high or low selection switch 174. The different concentrations can also be selected for delivery to the patient by merely pressing or toggling the high or low selection switch 174. After the heart is stopped with a high concentration, a lower concentration of arrest agent will maintain the still heart. The perfusionist can adjust the low level of arrest agent separately and then during operation can select a low arrest agent supply to the patient. Switching from high to low and back again is advantageously a one-button procedure.

After the blood-to-crystalloid ratio is established and a flow rate begins with or without an arrest agent, a surgeon may determine that an additional additive should also be included within the cardioplegia solution. For this purpose, the additive may include one or more medicinal solutions or compositions and the option for controlling the addition of this additional additive is provided with a display area 184, including an adjustment activation switch 186, a digital display 188 and an on or additive included light 190. When the value in display 188 is zero, the light 190 is off and when it is greater than zero, then light 190 comes on to indicate to the perfusionist and those observing the control panel display that an additive is being included.

Once the solution is complete as to its composition, then it will be heated or cooled depending on the requirements of the particular phase of the heart operation. Typically, during a myocardia procedure, the heart will be cooled with a cold bath during the operation and will be warmed subsequent to the operation in order to revive operation of the heart. Depending on the protocol of the operation involved, various phases of heating and cooling of the heart may be required. The heat exchange or display area 192 includes a switch 194 by which the temperature of the warm bath or the temperature of the cold bath may be alternatively detected and viewed at display 196, which is associated with an understandable label 198. A delivery temperature adjustment switch 200 is provided which upon depressing engages the set knob 160 and lights up the set light 158 to adjust the desired delivery temperature which is display in a digital display 202. A label 204 is provided adjacent the digital display 202 and preferably, is on or associated with the adjustment switch 200 which indicates that this digital display is representative of the delivery temperature. Again, when the delivery temperature adjustment switch 200 is activated, it will become lit and digital display 202 will increase the light intensity so that the perfusionist will immediately understand that adjustment using knob 160 is directed to the delivery temperature.

Another characteristic of the system which advantageously provides information to the perfusionist is the system pressure such that a system pressure display area 206 is provided with a digital display 208 and a label 210. Normally, the system pressure depends upon the flow rate and the patient pressure, as well as with the particular configuration of the system. An inordinately high system pressure can indicate a kink in a tube or other potential problems. For example, where the system pressure is substantially higher than the delivery pressure, then in that event, there may be a risk that through movement of the delivery tubing an obstruction may be alleviated which will result in temporarily excessive pressure to the patient. The perfusionist can be on guard for such a situation and be ready to respond for the safety of the patient.

A preferably adjustable key characteristic or parameter of the system is the patient delivery pressure. This may be measured at a catheter or cannula at which the system is connected to the patient's blood vessels. A readout of the patient delivery pressure is included within a delivery pressure display area 212. A digital display 214 with an appropriate label 216 is provided. Preferably, both the flow rate display 164 and the delivery pressure display 214 are centrally located for ease of observation and the attention of the perfusionist as they are substantially key characteristics of the system. Also preferably, the flow rate display 164 and the pressure display 214 are larger than the other subcharacteristic displays so that attention is immediately drawn to these features without undue "hunting" by the operator. It will be understood that for any given patient and system set-up the flow rate and delivery pressure of the system are inter-related. Thus, for a given set-up, tubing size and integrity of the connection or catheterization to the patient, increasing the flow rate will normally increase the pressure. If there are restrictions in the flow path, it will be more difficult to move the same amount of cardioplegia fluid through the same tubes and blood vessels. This will tend to cause both a lower flow rate and a higher pressure.

Controls for such a system will operate according to these principles, for example, if a lower pressure is required, a lower flow rate must be set. If a higher pressure is required, a higher flow rate must be requested. However, if a change in the system occurs, such as a restriction at the delivery catheter, the pressure will tend to increase and the flow will tend to decrease. If a constant flow is requested, only the pressure will go higher. If a constant pressure is requested, the flow rate must be decreased.

Figure 3:
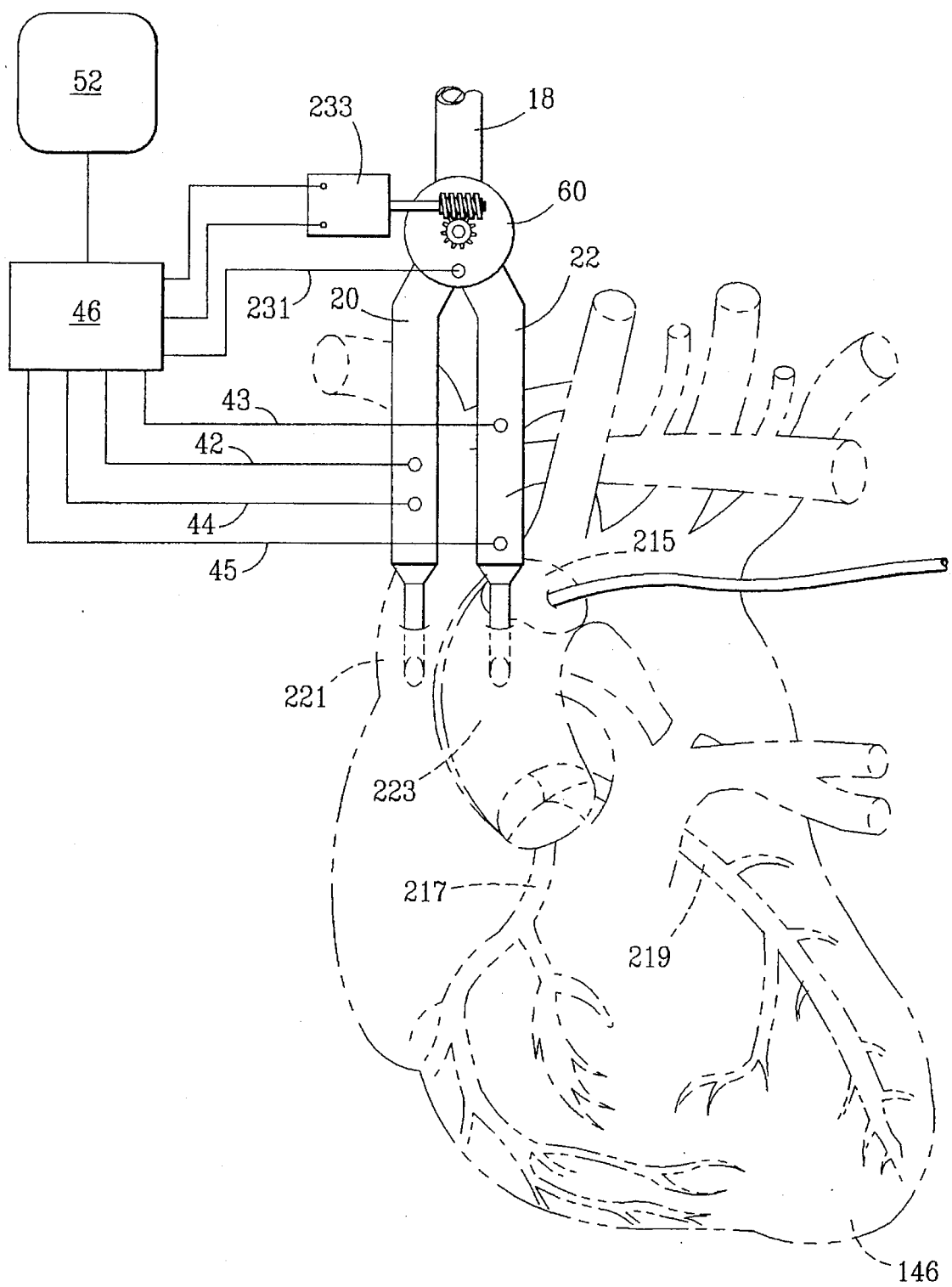
FIG. 3 is a schematic plan view of a simplified cardioplegia system connected for selectable antegrade or retrograde fluid flow.

Also important in the delivery of blood mixture fluid, and particularly cardioplegia fluid to a patient, is the direction of blood flow through the blood vessels. A schematic depiction of a directional valve connected to antegrade and to retrograde catheters to a heart is depicted in FIG. 3. Antegrade flow through the blood vessels of the heart is the normal blood flow direction with the cardioplegia solution entry through the aortic root 215 or the coronary ostia, flowing in through the coronary arteries 217 and 219, through the muscles, and out through the veins. Alternatively, the cardioplegia solution may be delivered in a retrograde fashion through a catheter 20 engaged in the coronary sinus 221 so that the cardioplegia solution is pumped into the veins, back through the muscle tissue and out from the arteries. Typically, the retrograde flow of cardioplegia fluid is desirable when there is substantial coronary blockage so that the tissues adversely affected by the arterial blockage will receive or have a chance of receiving cardioplegia solution while the blockage is bypassed during the surgery. In any event, the acceptable pressure for the system in the antegrade direction is different than the acceptable pressure in the retrograde direction. In the antegrade or normal direction of blood flow, the coronary arteries are thick walled vessels accustomed to normal systemic blood pressure ranges, typically exceeding 100 mm Hg; therefore, to achieve normal distribution, high perfusion pressures are necessary. Conversely, in the retrograde direction, the cardioplegia solution is delivered via the coronary sinus into the coronary veins. The coronary sinus and coronary veins are thin walled vessels accustomed to low pressures, typically less than 20 mm Hg; therefore, it is dangerous to expose these vessels to the high pressures required for antegrade delivery. Surgeons change the direction and pressure of delivery to achieve optimum distribution of cardioplegia solution. Because of the different delivery scenarios, it is advantageous to have a system control panel which is intuitive by logical depiction of the system flow paths.

A visual display is provided in which indicators 220 and 222, such as an indicator light 220 indicating retrograde flow and an indicator light 222 indicating antegrade flow will be activatable by the perfusionist depending upon the system connections and catheterization of the patient. There is also a retrograde adjustment switch 224 and a retrograde flow "on" light 226, as well as an antegrade adjustment switch 228 and antegrade flow "on" indicator 230. In a preferred embodiment, flow lights 226 and 230 are dynamic or animated indicators which have flashing or a sequentially illuminated series of lights which give the appearance of movement toward the heart along the flow path corresponding to the operating mode of the system at the time. If the flow stops, the dynamic lighting or animation of flow also stops; this condition is immediately perceivable by the perfusionist or the surgeon. The function of the retrograde switch 224 and the antegrade switch 228 will be discussed more fully below with various preferred embodiments. Initially, in a basic mode the switches 224 and 228 are provided so that the perfusionist can select from the panel which flow direction is to be displayed. The selection of the flow direction may depend upon the indication from the surgeon which direction is activated by the surgeon. Activation of the switch by the perfusionist will activate different sets of default limits and alarms and as the delivery pressure displayed at 214 is typically a reading which is detected at the entry catheter, whether in the aortic root or in the coronary sinus, so that appropriate input to the display 214 is determined by selection switches 224 or 228.

In further preferred embodiments, the patient is connected for either retrograde or antegrade flow with a cardioplegia diversion valve 60 interposed so that the surgeon may select between antegrade or retrograde flow during surgery. The antegrade switch 228 and the retrograde switch 224 may in the preferred embodiment be connected at sensor 231 to detect the position of the valve 60 automatically and toggle between the appropriate positions. Alternatively, actuation of switches 224 or 228 by the perfusionist may actually be connected to control section 46 for actuation of a servo motor 233 for controlling the position of the valve 60 so that it can be caused to move from the control panel 52, between retrograde and antegrade flow directions as desired. As with each communication connection between the display panel 52 and control mechanisms for the system 10, the signals may be electrical signals carried by wire, radio signals transmitted between the panel, the control circuitry 46 and/or the various control mechanisms.

During surgery, it is advantageous to continuously monitor the operation of the system. It is also advantageous to allow the perfusionist a certain degree of freedom to attend to various matters, such that alarm limits may be set. A limit display section 232 is advantageously provided in which an upper limit display 234 and a lower limit display 238 are provided. Initially, the upper and lower limits are set by default or by the perfusionist to establish maximum and minimum safe patient delivery pressure. The actual pressure corresponding to the pressure at display 216 and the actual flow rate is advantageously depicted with an analog pressure display 246, which is positioned between the upper and lower limit digital displays 234 and 238. The perfusionist can visually observe the relationship of the patient delivery pressure as digitally displayed at display 216 in relationship to the upper and lower limits. A lighted label 248 is provided in the analog display area 246 to clearly indicate which limits are being observed.

The safe limit will potentially be different for antegrade flow or for retrograde flow directions. Setting limits separately, depending upon flow direction, may be accomplished with retrograde adjustment switch 242 and with antegrade adjustment switch 244. Depression of either switch 242 or 244 will activate the set knob 160 so that the upper and lower limits can be adjusted for each flow direction. It is noted that the operator may view the limits separately for the antegrade and the retrograde flow direction. However, in a preferred embodiment, as will be described below, the control panel 52 automatically displays the appropriate limits depending upon the flow direction indicated at 220 or 222.

Figure 4:
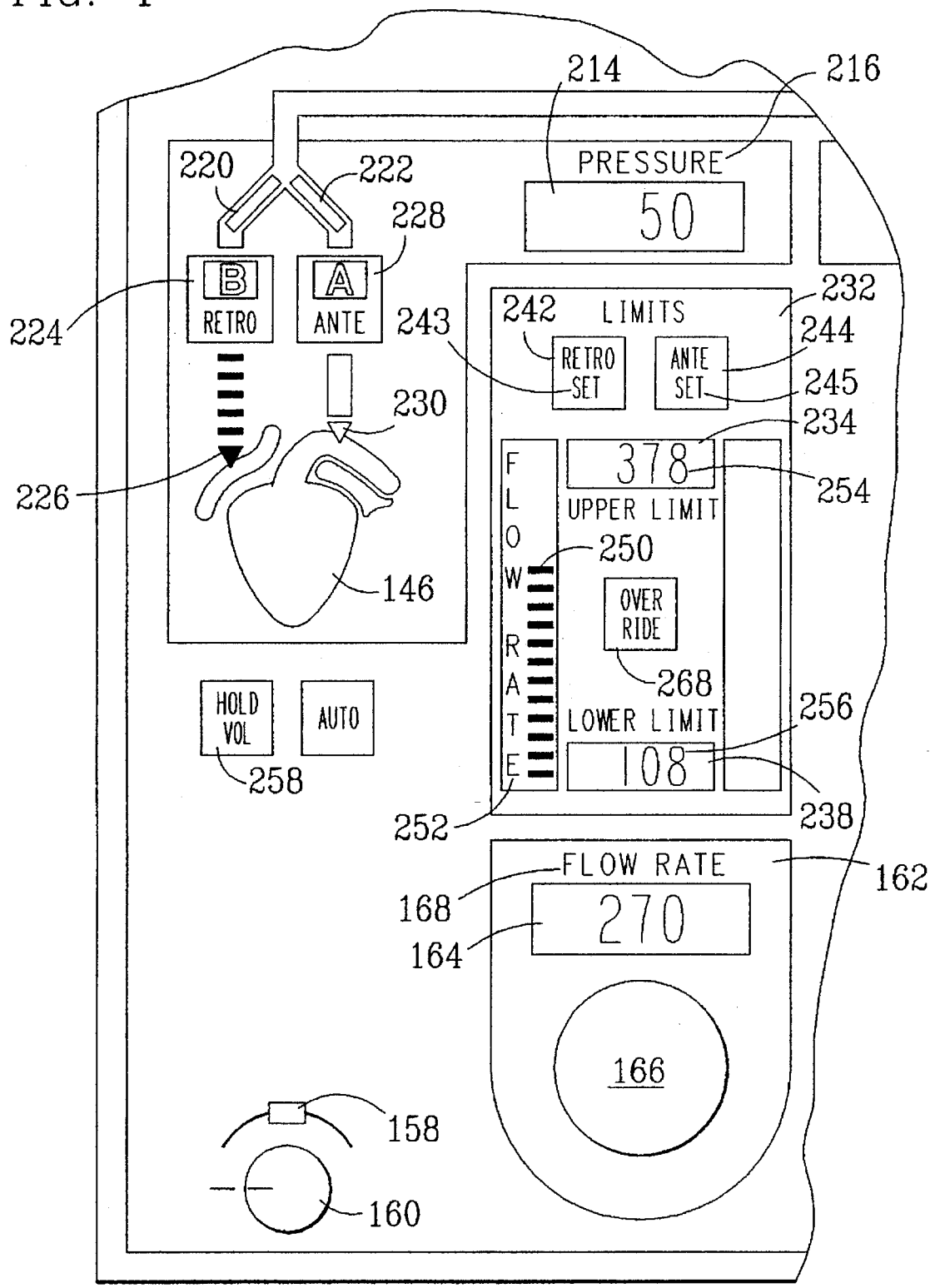
FIG. 4 is an enlarged view of a portion of the display panel including digital limit displays and analog displays of system operating parameters relative to the limits.

As shown more clearly with reference to FIG. 4, the same display area upper limit 234 and lower limit 238 can be used in connection with a flow rate limit display in which an analog display 250 of the actual flow rate is provided and has a lighted label 252 to clearly indicate that the upper flow rate limit 254 is activated and the lower flow rate limit 256 is activated. Again, the upper and lower flow rate limits can be separately set by the operator or by the control section 46 for retrograde and for antegrade flow through the patient's heart. The antegrade switch 244 and retrograde switch 242 may be used to separately display and/or set the limits. In the normal operation of cardioplegia deliver, the perfusionist has control over and adjusts the flow rate with knob 166. This condition is preferably the default condition during the normal run mode.

It has been found advantageous, during surgery and during continuous operation of a cardioplegia delivery system in the run mode, to maintain a desired constant pressure. As pressure for a given cardioplegia system is dependent upon and proportional to the flow rate, automatic microprocessor control of the flow rate can be programmed in order to maintain a desired pressure. Some of the advantages of a constant pressure delivery system include the prevention of excessive pressures which can cause physical damage to the heart, and the use of upper and lower flow rate limits to ensure adequate delivery to the heart tissues. For example, it is not unusual for the retrograde cannula to become dislodged from the coronary sinus, resulting in delivery of the cardioplegia solution to the right atrium rather than to the heart tissues. In the existing systems, the surgeon must rely on periodic visual monitoring of pressure to ensure that the catheter is in place. With the use of upper and lower flow rate limits the instrument microprocessor will immediately detect a result in pressure caused by the dislodged cannula and attempt to compensate by increasing flow rate. When it is "evident" to the microprocessor, as through preprogrammed limits or algorithms, that pressure cannot be maintained within the limits of flow rate, the instrument will sound an alarm, alerting the perfusionist and surgeon to the problem.

In a method of operation of the instrument according to the present invention, the perfusionist will ramp up flow rate by manually adjusting flow rate knob 166 until a desired pressure is achieved. After the flow rate is established at a more or less steady state at which a desired pressure or desired range of pressures is being maintained, then the perfusionist may, in a preferred embodiment, activate an automatic pressure maintenance mode with switch 260. The flow rate would then be automatically varied to keep the existing desired pressure. The upper and lower pressure limits would no longer be appropriate. The appropriate limits would be those of the flow rate. Upper and lower flow rate limits may be set by the perfusionist or preferably, according to one embodiment of the present invention, may be automatically established based upon a calculated relationship between the existing pressure and existing flow rate at the time the automatic mode is activated and the existing or preset upper and lower pressure limits.

The upper and lower limits are established to activate various alarm systems which in the preferred embodiment will include a period of flashing displays, such as a flashing upper limit when the upper limit is approached or a flashing lower limit when the lower limit is approached. This might be used in conjunction with an audible alarm. Alternatively, an audible alarm may be initiated after a given time period of warning flashing. Subsequent to a warning alarm in combination with the flashing lights, the system may be turned off and then automatically move into an inactive mode unless an override switch 268 is activated. The alarm condition may also be depicted on an information/time display screen 270.

Information/time display screen 270 is advantageously included on or adjacent to the same face 140 of display 52. The information/time display screen 70 may include a large LED screen with multiple display fields, such as information display column 272 and 274. The information/time display screen 270 may also be provided in combination with a plurality of soft keys 276, 280, 284 and 288.

Soft key 276 is configured adjacent to, and informationally corresponds to, information field 278. Soft key 280 is correspondingly located adjacent information field 282. Soft key 284 is adjacent to information field 286. Soft key 288 is adjacent to display field 290. Additional soft keys 291 and 292 are provided for use in connection with optional system configurations, the substance of which is beyond the scope of the present invention.

In the preferred embodiment, there are also designated function or mode keys provided in association with information display screen 270, such as a switch, key or button 293, for entering into a priming mode by which the system is primed with appropriate component solutions. A particular timer mode switch 294, a volume function switch 295, a calibration mode switch 296 and a defaults mode switch 297. The operation of controls, such as microprocessor 46 and various modes of operation will be described more fully below.

Generally, the primary modes of operation will advantageously include a "set-up" mode; a system priming mode; a run mode; a defaults mode; a time mode; a volume function mode; and a calibration mode. The method of operator interaction with the invention display panel and the controls associated with the control panel will be more fully described with reference to FIGS. 5–11 below.

With reference to FIG. 5 is a schematic flow chart for the display panel 52 operating in connection with the controls, such as with a microprocessor 46 in a set-up mode. Throughout the flowing description of the flow charts of FIGS. 5–11, the language depicted in the drawing blocks for each step is an example of the informational readout, which in one preferred embodiment, will appear in an LED information/time display screen 270, which as discussed above, is preferably associated with the display panel 52, positioned adjacent to but separate from the flow path 142.

When power is initially turned on, the display panel 52 and associated instrument controls 46 run internal diagnostic tests. While running the diagnostic tests, no switches, buttons or soft keys are activated by the operator unless there is an aspect of the tests which required attention from the operator. Preferably, the information/time display screen 270 will display the tests which are being performed as they are undertaken. Previously stored parameter values for the system, such as default values for the controllable characteristics of the cardioplegia delivery system will be displayed as appropriate. Any problems discovered will be displayed and preferably, the user will be prompted with appropriate instructions and/or inquiries for determining and/or affecting corrective procedures, if available.

Following initial power-up and testing, the display panel 52 and controls system 46 automatically enter an initial "set-up" mode. During the initial set-up mode, all of the digital displays which are preferably positioned along the displayed logical flow path 142 will display default values. Preferably, the default values are displayed in a relatively dim intensity. If a default value is zero, it is not displayed, and that parameter is skipped during set-up.

The information/time display screen 270 prompts the user to provide information by "asking" with an appropriate preprogrammed written question whether this is a new case. If it is a new case, the user presses one of the soft keys 276, 280, 288 or 284 in one of the display fields 278, 282, 286 or 290 which is positioned adjacent a "yes" appearing on the display screen 270. Alternatively, if it is a continuation of a case, the user is prompted to press another one of the soft keys adjacent to a "no" appearing in one of the display fields of the display screen 270. In the presentation shown at step 301 of FIG. 5, pressing the "yes" key 276 acts to reset the volume and dose total, after which set-up continues. When the "no" key 288 is depressed, then controls return to a "run" mode, a description of which begins at steps 330 below with reference to FIG. 7.

If it is a new case (i.e., a different patient or medical operation) then set-up continues and a "change default" screen will appear in display screen 270 as at 303 and the controls will be set to allow the user to change the default settings before continuing through set-up. Any zero default values which would not have been displayed during the set-up mode can be changed to a desired value. To change default settings, the user presses a soft key 280 corresponding to a "yes" response to screen 303 and enters the defaults mode at step 335 as described below in connection with FIG. 7. The default mode could alternatively be entered directly using default key 297.

If the existing default values are to be used, then the "no" response is entered via the soft key 284, which is depressed to continue with set-up beginning at the next step 304.

In the initial set-up mode, a crystalloid volume screen will be presented on the information screen 270 of display panel 52, which, for example, may appear as indicated in the box at 304. Also, above the set knob 160 the LED display 158 shows that the "set" mode has been activated. The user rotates set knob 160 to scroll through a list of possible selections. The scrolling list will preferably appear on screen 270. For example, the instrument may be provided with crystalloid supply containers having a variety of capacities in increments of 500 or 1,000 units. The size of the crystalloid supply container which is connected to the system by the perfusionist is selected when it appears on screen 270 by pressing the soft key 284 to confirm the selection. Confirming the selection also turns off the set light 158 above set knob 160.

Upon selecting the crystalloid volume, the display automatically moves to the set-up screen for blood:crystalloid ratio as depicted at step 305 in FIG. 5. Again, the set light 158 above the set knob 160 comes on. Also preferably, the blood:crystalloid ratio switch 150 becomes lighted and display 152 is preferably brightened to indicate to the user that the set knob is to be used to set the blood:crystalloid ratio and that the digital display 152 above the blood:crystalloid ratio button 150 will be displaying the values which may be selected. Preferably, the value displayed in the digits at the blood:crystalloid ratio digital display 152 will be enhanced in brightness over the brightness for default values or over the brightness for the display 152 during run mode. All of these visual clues emphasize to the operator that it is the blood:crystalloid ratio which is to be set and confusion is reduced to a minimum. The user changes the value of the ratio with the set knob 160. Upon reaching a desired ratio, the value is confirmed by pressing the blood:crystalloid ratio switch 150. The displayed digits at 152 go back to a dim intensity, the blood:crystalloid switch light goes out, and the set legend 158 above the set knob light 160 goes out. When setting the blood:crystalloid ratio, the ratio initially depicted will be a previously existing default value. If the default value is to be maintained, then the operator may confirm that selection by merely depressing or actuating the blood:crystalloid switch 150. This confirmation procedure is simple yet, as a safety precaution, it requires the operator to actually reach and confirm the previously existing default value whenever the instrument goes through the set-up mode.

Subsequently, the instrument display and controls move automatically into the initial set-up for the arrest agent source units selection screen at box 306. The set legend light 158 comes on. The user scrolls through a list of possible selections which are displayed on the display screen 270 using set knob 160. The selected source units may correspond to available incremental values of arrest agent supply containers. Confirmation of the actual size of the source unit container is accomplished by pressing a soft key or button 284 which will act to turn off the set light.

Next, the initial set-up arrest agent source concentration selection screen 307 appears. Again, the set legend light 158 comes on above the set knob 160. A default value, if any, is displayed and the user uses the set knob to change the value, if desired. In connection with concentration selection, the units will have been established by the arrest agent source 284 units selection screen in step 306 above. The operator presses soft key 284 to confirm the value, which turns off the set light.

The instrument moves automatically into the set arrest agent delivery concentration selection screen at step 308 and the set legend light 158 comes on above the set knob 160. The arrest agent switch light 172 also comes on. Initially, the arrest agent "high" value is displayed at digital display 178. The high arrest agent delivery concentration value is preferably displayed with bright digits. The previous default value, if non-zero, will initially be displayed. The units corresponding to the digital display are determined by the selection made for the arrest agent source unit in step 306 above. The user uses the set knob 160 to change the value for the high arrest agent delivery concentration and presses the agent switch 172 or the high/low switch 174 to confirm the value.

Either switch 172 or 174 acts to move the instrument to the initial set-up low arrest agent delivery concentration screen 309 and the set legend light 158 stays on from step 308. The arrest agent switch light 172 stays on; however, the bright, or high intensity, LED display returns to a lower intensity. The low arrest agent delivery concentration value is displayed at 178, preferably in bright digits. The units are again determined to correspond to the units selection in step 306 above. The user uses the set knob 160 to change the value displayed and by depressing the arrest agent switch 172 or by pressing the high/low switch 174 to confirm the displayed value. The arrest agent switch light 172 goes off, the set legend light 158 goes off and the low LED light goes off, the high LED light comes on. However, the high arrest agent delivery concentration value is displayed at 178 in dim digits. If the value is non-zero, then an insertion LED light 182 comes on, indicating that the arrest agent will be entering into the cardioplegia fluid flow path. This advantageously visually prompts the operator to understand that an arrest agent at the indicated high concentration is set to be supplied, thereby avoiding confusion as to whether an arrest agent is being used in connection with the cardioplegia display system and what concentration is to be initially supplied.

The instrument moves automatically to the initial set-up of step 310 for selecting additive source units. A source unit selection screen 310 is presented on display screen 270 and the set legend light 158 comes on. The user scrolls a list of possible unit selections, using the set knob 160. The unit selection is confirmed pressing a variable function soft key 284 and also the set light 158 is turned off. Once the additive source unit is selected and confirmed, then the instrument moves automatically to additive source concentration selection screen 311 in display screen 270. The set legend light 158 again comes on. The user uses the set knob 160 to change the value, if desired. The units are determined by the selection made for the additive source unit in step 310 above. Pressing the variable function (VF) soft key 284 corresponding to the "confirm" display in field 286 on the display screen 270 will confirm the displayed value and will turn off the set light 158.

The instrument moves automatically into the additive delivery concentration selection screen 312 and the set legend light 158 comes on above the set knob 160. The additive switch light 186 also comes on. The additive delivery concentration value will be displayed in bright digits at display 188. The units, of course, are determined by the selection made during the additive source unit selection in step 310 above. (For example, delivery units=source units+by 1,000). The user uses the set knob to change the value, if desired. Pressing the additive switch 186 confirms the value. Upon confirming the value, the additive switch light goes off, the additive delivery concentration value will be displayed in dim LED digits. If the value is non-zero, then the appropriate insertion LED arrow indicator light 190 comes on, indicating that there will be an additive entering into the cardioplegia fluid flow path 142 so that the operator is visually prompted and the potential for misunderstanding or for confusion is reduced.

Continuing in the initial set-up mode, the next step will be the warm temperature selection step 313, in which the set legend light 158 comes on. Also, the delivery temperature switch 200 light comes on, lighting up the display 204. The warm/cold switch 194, the warm LED light indicator 193 comes on. The warm delivery temperature value is displayed in bright digits, such as LED digits, in display 196. The set knob 160 is used to change the value. Pressing the delivery temperature switch confirms the value and the delivery temperature switch light goes off; the warm delivery temperature value is displayed in dim LED digits; the warm LED light stays lighted; and the set legend goes off.

Next in set-up step 314, a maximum retrograde pressure limit selection screen is presented. The set legend light 158 comes on. The retrograde set switch 242 and LED light 243 come on. The maximum retrograde pressure limit value is displayed in upper limit display 234 in bright digits, preferably bright LED digits. The user changes the value with set knob 160. Pressing the retroset switch confirms the selected value and the maximum retrograde pressure limit is displayed at 234 in dim LED digits.

The minimum retrograde pressure limit selection screen 315 comes on automatically in the initial set-up procedure. The set legend stays on from the previous step 314. The retrograde set LED 243 stays on. The minimum retrograde pressure limit value is displayed in bright LED digits at 256. The user changes the value with set knob 160. Pressing the retrograde set switch 242 confirms the value; the retroset LED light 243 goes off. The set legend light goes off and the minimum retrograde pressure is displayed in dim LED digits at 238.

Next in the initial set-up mode, a maximum antegrade pressure limit selection screen 316 is displayed. The set legend light 158 comes on. The antegrade set LED light 245 comes on, illuminating switch 244. A maximum antegrade pressure limit value is displayed, preferably with bright digits, such as LED digits, in upper limit display 234. The user changes the value with set knob 160. Pressing the antegrade set switch confirms the value and the maximum antegrade pressure is displayed in dim LED digits at 234.

Next, the minimum antegrade pressure limit selection screen 317 comes on. The set legend stays on from step 316. The antegrade set LED light 245 also stays on. The minimum antegrade pressure limit value is now displayed in bright digits at the lower limit pressure display 258. The user changes the value with set knob 160. Pressing the antegrade set switch 244 confirms the value, turns off the antegrade set LED 245, turns off the set legend light 158 and the minimum antegrade pressure limit changes from a bright display to a dim display at lower limit display 258.

Next in the preferred embodiment of the present invention, a disposable cassette is used in the pump. The next step 318 presents a pump disposal screen. A message is displayed if the pump disposal is not in place as detected by the instrument with a detection mechanism (not shown) after all the set-up parameters have been confirmed.

Next, an insert additive pouch screen 319 message is displayed if an additive pouch is not in the instrument when all the set-up parameters have been confirmed.

An insert arrest agent pouch screen 320 displays an appropriate message if an arrest pouch (i.e., a container supplying the arrest agent) is not in the instrument when all the set-up parameters have been confirmed.

An appropriate message as with the insert heat exchanger screen 321 is displayed if the heat exchanger is not appropriately connected to the instrument when all the set-up parameters have been confirmed.

A set-up complete screen 322 displays an appropriate message when the instrument has completed the set-up mode. All of the VF soft keys, all of the function keys and the control panel switches become operative. The instrument is ready to be primed.

With reference to FIG. 6, the instrument priming mode (or prime mode) is entered by pressing the prime function key 293. The user is prompted at screen 322 of FIG. 5 to activate the prime mode, with a phrase such as "ready to prime." Upon entering the prime mode, a circulating water screen 323 message is displayed at the display screen 270. The message continues to be displayed during water priming. A timer digitally counts down on screen 270 until water prime is completed or stopped. The user may stop the water primed by pressing a VF soft key, such as key 284 adjacent a stop instruction in field 286. If the stop VF soft key is pressed before priming is complete, the system will move to a priming incomplete screen 329, as discussed below. If the prime mode continues and if the instrument detects a low water level during prime, a fill water reservoir screen 324 will be displayed. The reservoir (not shown) must be filled for priming to continue. No other switches or keys will be active until the water reservoir is sufficiently filled and the fill condition is detected by the instrument.

After the countdown is complete, a water circulation completed screen 325 will display an appropriate message display at display screen 270. At this point, the water prime is completed and the user will be prompted with an appropriate message to prime the cardioplegia system. The user uses a VF soft key 280 adjacent a positive response display end field 282 in order to select cardioplegia priming. The user may alternatively select not to prime the cardioplegia at that time by pressing VF soft key 284 adjacent a negative response displayed in field 286. If the positive response is selected, then the cardioplegia screen 326 is displayed. If the response is negative, then the priming incomplete screen 329 is displayed.

At step 326, the message indicating that cardioplegia priming is taking place is displayed. A timer counts down until the cardioplegia priming is completed or until it is stopped. The user may stop the cardioplegia priming by pressing a stop VF stop key, such as key 284.

During priming, the instrument detects whether the blood line is connected. If the blood line is not connected, a no blood available screen 327 is displayed. The user may continue cardioplegia priming by connecting the blood line and pressing the continue VF soft key 280. Priming can be terminated by pressing the exit VF soft key 284.

Also during priming, the instrument detects whether the crystalloid line is connected. If the crystalloid line is not connected, a non crystalloid available screen 328 displays an appropriate message with an instruction to connect the crystalloid line. The user may continue cardioplegia priming by connecting the crystalloid line and subsequently depressing the continue VF soft key 282. When the continue soft key is depressed, the system returns to the priming cardioplegia screen 326 and reinitiates the time countdown for priming to be completed. Alternatively, the user may exit the priming mode by pressing the exit key 284, in which case the system returns to set-up complete step 322 and prompts the user to begin the priming procedure over again.

If priming is stopped before completion, either during step 323 or step 326, then the priming incomplete message screen 329 is displayed. The user may resume priming by pressing the continue VF soft key 280 and resume priming of either the water which will return the system to circulating water screen 323 or to the priming cardioplegia screen 326, depending upon which step was underway when the priming was stopped. Priming can be terminated when the priming incomplete screen is displayed by pressing the exit VF soft key. Pressing the exit key returns the system to step 322 prompting the user to begin priming.

If priming is completed both with respect to the water and cardioplegia, then the instrument moves into the run mode, which will be described in connection with FIG. 7. In the run mode, a run mode screen 330 is displayed at 270. The run mode screen displays certain time dependent information useful to the perfusionist. For example, in the preferred embodiment, the primary run mode screen 330 displays the delivery time which is preferably a cumulative delivery time for the particular patient. An off time is also displayed, which is preferably the off time since the last delivery of cardioplegia solution to the patient. Incremental volume of the cardioplegia solution delivered may be depicted and also a display indicating the remaining amounts of crystalloid, arrest agent and additive may be displayed. Preferably, an analog display of the remaining crystalloid, arrest agent and additive may be displayed to facilitate the user's quick understanding of the condition of the cardioplegia delivery system at a glance. When the delivery time is detected and accumulated based upon flow starting and flow stopping. The off time is also determined through detection of the flow stopping and flow starting. When delivery is started by turning the flow knob 166, the delivery time begins incrementing and accumulating. When the flow is stopped, as by turning flow control knob 166 so that the flow rate displayed at 164 is zero or if the system otherwise shuts down due to reaching excess limits or the like, then the delivery stops accumulating but remains displayed, the off time resets to zero and begins incrementing. When the flow is started again, the delivery time begins accumulating from the time previously displayed and the off time continues to be displayed. If delivery is interrupted again, then the off time resets to zero and begins incrementing and remains displayed when delivery is started again. Thus, the delivery time will represent a cumulative delivery time and the off time will be the duration of the most recent period of interrupted delivery. The off time incrementing does not begin until after the first delivery.

When the system is in the run mode, various messages may be displayed to notify the user of the system's inability to monitor antegrade flow rate limits or antegrade pressure limits, or alternatively, retrograde flow rate limits or retrograde pressure limits. Thus, screen 331 will provide a message to indicate that the flow rate limits cannot be monitored because of no transducer input available to the instrument. The user must supply a transducer and connect it to the system or zero the limits or the system will continue. If there is no transducer input available to the instrument, then an appropriate antegrade transducer/pressure limit screen 332 will be displayed. The user must supply the pressure transducer input or zero the limits before the system will continue to operate in the run mode. Similarly, retrograde/flow rate limit screen 333 will be presented if the flow rate limits cannot be monitored because no transducer input is available. The user must supply flow rate transducer input or zero the limits. A retrograde/flow rate pressure limit screen 334 will be presented if the limits cannot be monitored because no transducer input is available to the instrument. The user must supply the pressure transducer input or zero the limits. Zeroing the limits or requiring the transducer input is provided will avoid conditions where the operator is under a mistaken impression that upper and lower limits are being monitored by the instrument when no transducer input or inadequate transducer input is being provided so that the instrument can provide the limit monitoring functions.

FIG. 8 depicts a schematic flow diagram for use in a defaults mode. The user enters and exits the defaults mode by pressing the defaults key 297 or enters during the set-up mode as previously discussed in connection with FIG. 5 above.

When the instruments entered into a defaults mode, screen 335 is depicted prompting the user to select a parameter for which the default value is to be set or changed. The user selects the parameter to be changed by pressing the appropriate parameter switch on control panel 52. For example, parameter switch 150 allows change in defaults for the blood:crystalloid ratio; parameter switch 172 allows change in the arrest agent; parameter switch 186 allows changing the default for additives; parameter switch 200 allows changing the defaults for the delivery temperature; parameter switch 242 allows defaults for the retrograde upper and lower flow limits; and parameter switch 244 allows antegrade upper and lower limits. Upon depressing one of the selected parameter switches, the selected switch light comes on and the digital displays display the default values in bright LED digits. The "set" legend light 158 comes on and the user can change or select the desired value using set knob 160. To confirm a new value, the user presses the parameter switch which toggles the switch to the off position, turns the switch light off, turns the set legend off, and changes the LED digits from a bright display to a dim display. After the user is through changing default values, he or she may exit and save the default values by pressing the save VF soft key 284. If the user wishes to return to the old default value before the updated defaults are saved, the user may press the undo VF soft key 280, which will restore the pre-updated default values and leaves the user in the default mode with default screen 335 displayed at screen 270. If the user entered the defaults from the set-up mode, the user will return to the set-up mode. If the user wishes to exit the default mode, depressing the default function key 297 will leave the default mode. If the entered values have not been saved, the user will be prompted to save the new values or to undo the values before leaving the default mode. If the user entered the defaults mode from the set-up mode, the system will be returned to set-up. If the user entered the defaults mode from the run screen, the user will be returned to the run screen.

By way of example, in the defaults mode if the blood:crystalloid ratio parameter button 150 is depressed, screen 336 will be displayed. The set legend light 158 comes on and the set knob 160 is activated. The blood:crystalloid ratio set light comes on and the blood:crystalloid ratio value is displayed at display 152 in bright LED digits. The user may change the value using set knob 160. Confirming the defaults value requires pressing blood:crystalloid ratio switch 150. The LED digits go back to a dim intensity. The blood:crystalloid switch light goes off and the set legend light 158 goes off. If the user wishes to refill the crystalloid supply, the user presses the refill crystalloid soft key 280 before pressing the blood:crystalloid switch 150 to confirm. If the crystalloid supply is replenished, then the system will move to screen 344 as described below to appropriately enter the new crystalloid volume.

In another example, in the defaults mode if an alternate arrest agent delivery concentration is to be re-set, the arrest agent switch 172 is depressed and high/low switch 174 is toggled until the low LED indicator light 175 comes on. The set legend light is on. The low arrest agent delivery concentration value is displayed in bright LED digits at display 178. The units are the same as for the high arrest agent delivery concentration. The user changes the value with set knob 160. Pressing the arrest agent switch 172 or the high/low switch 174 confirms the value, turns off the arrest agent switch, turns off the set legend light, turns off the low LED indicator light and turns on the high LED indicator light 173 and displays the high arrest agent delivery concentration in dim LED digits. It can be seen that basically the same procedure for setting a desired value for any of the available adjustable characteristic parameters of the system can be accomplished substantially as described above with respect to the set-up mode steps 305, 308, 309, 312, 313, 314, 315, 316 and 317. Upon saving or undoing the changes in the default values for the parameters and exiting the defaults mode with switch 297 returns the user to the point of entry, whether in the set-up mode or the run mode.

Other information screens and programmable aspects may be called up with the function keys. For example, as shown in FIG. 9, a total volume screen as set forth at step 338 may be displayed by depressing the volume function key 295. This displays the total volume of cardioplegia solution delivered, the total blood volume delivered and the total crystalloid volume delivered. To reset the volume totals, the user depresses the soft key 284 which moves the user to screen 340 as discussed below. To review the amount or dose of arrest agent or additive which have been delivered to the patient, the user depresses the review dose soft key 280 which moves to screen 339.

The dose total screen 339 displays the total dose of the arrest agent and the total dose of additives which have been delivered to the patient. To re-set the totals, the re-set soft key 284 is depressed. To exit the volume mode, the volume function key 295 is depressed.

Whenever the re-set soft key is depressed while either the total volume screen 338 or the total dose screen 339 are being viewed, the volume re-set confirmation screen 340 will be displayed in display screen 270. This screen provides an appropriate message which requires the user to either confirm that the volume and dose totals are to be re-set or by depressing a confirmation soft key 280, or alternatively, allows the user to exit the volume review mode without resetting by pressing the exit soft key 284.

The user enters and exits a timer mode by pressing the timer function key 294. A first timer message screen 341, as shown in FIG. 10, is displayed in screen 270. The time mode may be used to control an incremental timer or to set a time for a countdown timer. To exit the timer mode, the user presses the timer function key 294. To start the incremental time, the user presses the start soft key 276. The incremental time is displayed. To stop the incremental timer, press the stop/re-set soft key 280 once. To re-set the incremental timer, press the stop/re-set soft key 280 twice if the timer is running or once if the timer is stopped. To set the countdown timer press the set soft key 284. The set legend light 158 comes on and the screen changes to second timer screen 342 as described below.

With the second timer screen 342, the set light 158 is on. The user changes the value using set knob 160. To confirm the value, the user presses the confirm soft key 284 and the set legend light goes out. The screen returns or changes to the first timer screen 341 as described above. The user exits the timer mode by depressing the timer function key 294 again.

Throughout the operation of the inventive cardioplegia display and control various warning screens may be displayed as shown in FIG. 11. For example, a crystalloid low warning screen is displayed when the instrument calculates that the amount of crystalloid remaining is low or below a predetermined threshold. The remaining volume is calculated based upon the volume of the supply and the amount which has been delivered to the patient based upon the blood:crystalloid ratio, the flow rate and the cumulative delivery time. When the amount is below a predetermined threshold level, the amount of crystalloid remaining will be displayed and no audible alarm is sounded. To refill the crystalloid, the perfusionist presses the refill soft key 284 which calls up screen 344 instructing the user to enter a new crystalloid volume as described below. To continue delivery without refilling, the user presses the continue soft key 280. If the delivery is continued, the message will reappear when delivery to the patient is stopped.

The refill crystalloid screen 344 allows the user to enter the volume of newly refilled crystalloid. A default value, such as for example, 1,000 milliliters may initially be displayed. The user may change this value by depressing the "change" mode soft key 280 which turns the set legend light 158 and activates the adjustment through set knob 160. To confirm the value, the confirm soft key 284 is pressed. To exit without entering a new crystalloid volume, an exit soft key 288 may be depressed. Upon confirming the new crystalloid volume or exiting the refill crystalloid screen, the user is returned to the run screen 330 as described above. An unable to deliver crystalloid screen 345 will be displayed to notify the user that all the crystalloid has been used. To refill crystalloid, "refill" soft key 284 is depressed which moves to the refill screen 344 as described above. To continue without crystalloid, the user may press the continue soft key 280. The blood crystalloid ratio display 152 automatically changes to 1:0 and the user returns to the run mode screen 330. An additive low warning screen 346 is displayed when the instrument detects that the amount of additive is below a predetermined threshold level. The amount of remaining additive is displayed. No audible alarm is sounded. To refill the additive, the user presses the refill soft key 284 which moves the system to the refill additive screen 347 as described below. To continue without refilling, the user presses the continue soft key 280 which moves the system back to the run mode screen 330. If delivery is continued, the message will reappear when additive delivery is stopped.

The refill additive screen 347 allows the user to refill the additive. After the additive has been refilled, the fill soft key 288 is pressed to move the system back to the run mode 330. To exit without refilling the additive, the user presses the exit key 284. Similarly, an arrest agent low warning screen 348 is displayed when the instrument detects that the amount of arrest agent is low or goes below some threshold level. The amount of remaining arrest agent is displayed. No audible alarm is sounded. To refill the arrest agent, the user presses the refill soft key 284. To continue without refilling, the user presses the continue soft key 280. If delivery is continued, the message will reappear when the delivery is stopped as by the user stopping delivery to the patient.

If the user depresses the refill soft key, a refill arrest agent screen 349 appears to allow the user to refill the arrest agent. After the arrest agent has been refilled, the user presses the fill soft key 288. To exit without filling the arrest agent, the user presses the exit soft key 284.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A blood mixture fluid delivery system, said system defining a fluid flow path from at least one source to a patient, said system having a display panel, a mechanism for infusing a blood mixture fluid to said patient along said fluid flow path and a control mechanism for controlling a plurality of controllable characteristics of said blood mixture fluid delivery system via a plurality of control elements located at a plurality of locations within said fluid flow path, said display panel of said fluid delivery system comprising:
   (a) a panel, having depicted thereon a visible schematic representation of said fluid flow path originating from at least one source, through said blood mixture fluid delivery system, to said patient; and
   (b) two or more visible displays, each visible display representing at least one of said plurality of controllable characteristics of said blood mixture fluid delivery system, each visible display taking a position with respect to said visible schematic representation analogous to a location of at least one associated control element within said fluid flow path.

2. A fluid delivery system as in claim 1 wherein one of said two or more visible displays comprises a flow rate display, positioned on said panel at a representative position along said visible schematic representation, for displaying a volumetric flow rate of said blood mixture fluid occurring at a corresponding path location in said fluid flow path.

3. A fluid delivery system as in claim 2 wherein said flow rate display include:
   (a) a digital display for digitally displaying said volumetric flow rate occurring at said path location; and
   (b) an analog display for visually depicting said volumetric flow rate occurring at said path location relative to a predetermined scale.

4. A fluid delivery system as in claim 3 wherein said analog display includes a number of linearly aligned, sequentially activatable LED indicators, wherein the number of LED indicators correspond to said predetermined scale.

5. A fluid delivery system as in claim 2 wherein said mechanism for infusing said blood mixture fluid to said patient further includes a pump activatable and controllable by said control mechanism to cause said blood mixture fluid to flow along said fluid flow path, wherein one of said two or more visible displays comprises a dynamic display indicative of pump activity.

6. A fluid delivery system as in claim 1 wherein one of said two or more visible displays comprises a pressure display, positioned on said panel at a representative position along said visible schematic representation, for displaying a pressure of said blood mixture fluid occurring at a corresponding path location in said fluid flow path.

7. A fluid delivery system as in claim 6 wherein said pressure display is for displaying a patient delivery pressure, wherein said path location is substantially adjacent to a point of infusion in said patient.

8. A fluid delivery system as in claim 6 wherein said pressure display is for displaying a system pressure, wherein said path location is distal to a point of infusion in said patient.

9. A fluid delivery system as in claim 6 wherein said pressure display includes:
   (a) a digital pressure display for digitally displaying said pressure occurring at said path location; and
   (b) an analog pressure display for visually depicting said pressure occurring at said path location relative to a predetermined scale.

10. A fluid delivery system as in claim 9 wherein said analog display includes a number of linearly aligned, sequentially activatable LED indicators, wherein the number of LED indicators correspond to said predetermined scale.

11. A fluid delivery system as in claim 1 wherein said two or more visible displays of said plurality of controllable characteristics, comprise:
    (a) an upper limit display selectable between displaying an upper flow rate limit or displaying an upper pressure limit;
    (b) a lower limit display for displaying a lower flow rate limit or displaying a lower pressure limit;
    (c) an analog rate display for displaying a measured volumetric flow rate within said fluid flow path, only upon selection of said upper and lower flow rate limit; and
    (d) an analog pressure display for displaying a measured pressure within said fluid flow path, only upon selection of said upper and lower pressure limits.

12. A fluid delivery system as in claim 11 further comprising:
    (a) a microprocessor operatively connected to said panel for automatically converting said upper and lower pressure limits to corresponding upper and lower flow rate limits based upon measured fluid pressure and measured volumetric flow rate; and
    (b) a automatic mode switch operatively connected for selecting said upper and lower pressure limit display and for activating said microprocessor to convert said upper and lower pressure limits to upper and lower flow rate limits based upon a measured volumetric flow rate and a measured fluid pressure measured when said automatic mode switch is actuated.

13. A fluid delivery system as in claim 1 wherein one of said two or more visible displays comprises a temperature display, positioned on said panel at a representative position along said visible schematic representation, for displaying a temperature of said blood mixture fluid occurring at a corresponding path location in said fluid flow path.

14. A fluid delivery system as in claim 13 wherein said temperature display is for displaying a system temperature, wherein said path location is in a heat exchanger fluid circulation path in said blood mixture fluid delivery system.

15. A fluid delivery system as in claim 13 wherein said temperature display is for displaying a patient temperature, wherein said path location is substantially adjacent to a point of infusion in said patient.

16. A fluid delivery system as in claim 1 wherein one of said two or more visible displays comprises a delivery indicator, positioned on said panel at a representative position along said visible schematic representation, for displaying whether the delivery of the blood mixture fluid is to a first path location or a second path location, said representative position, relative to said visible schematic representation, being analogous to said first and second path locations in said fluid flow path.

17. A fluid delivery system as in claim 1 wherein one of said two or more visible displays comprises an additive display, positioned on said panel at a representative position along said visible schematic representation, for displaying a quantity of additive in said blood mixture fluid at a corresponding path location in said fluid flow path.

18. A fluid delivery system as in claim 1 wherein said blood mixture is a cardioplegia fluid and said blood mixture fluid delivery system is a cardioplegia fluid delivery system.

19. A fluid delivery system as in claim 18 wherein one of said two or more visible displays comprises a flow rate display, positioned on said panel at a representative position along said visible schematic representative, for displaying a volumetric flow rate of said cardioplegia fluid occurring at a corresponding path location in said fluid flow path.

20. A fluid delivery system as in claim 19 wherein said mechanism for infusing said cardioplegia fluid to said patient further includes a pump activatable and controllable by said associated control mechanism to cause said cardioplegia fluid to flow along said fluid flow path, wherein one of said two or more visible displays comprises a dynamic display indicative of pump activity.

21. A fluid delivery system as in claim 18 wherein one of said two or more visible displays comprises a pressure display, positioned on said panel at a representative position along said visible schematic representation of said fluid flow path, for displaying a pressure of said cardioplegia fluid occurring at a corresponding path location in said fluid flow path.

22. A fluid delivery system as in claim 18 wherein one of said two or more visible displays comprises a blood-to-crystalloid ratio display, positioned on said panel at a representative position along said visible schematic representation, for displaying a ratio of blood-to-crystalloid in said cardioplegia fluid occurring at a corresponding path location in said fluid flow path.

23. A fluid delivery system as in claim 18 wherein one of said two or more visible displays comprise an arresting agent display, positioned on said panel at a representative position along said visible schematic representation, for displaying a quantity of arresting agent in said cardioplegia fluid at a corresponding path location in said fluid flow path.

24. A fluid delivery system as in claim 23 wherein said path location is where said arresting agent is introduced into said fluid flow path, said cardioplegia fluid delivery system providing,
(a) a means for delivering a user-definable high concentration of arresting agent or a user-definable low concentration of arresting agent from a single arresting agent source, and
(b) a means of adjusting such user-defined concentrations below and above such initial concentration settings during operation.

25. A fluid delivery system as in claim 18 wherein said two or more visible displays of said plurality of controllable characteristics, comprise:
(a) an upper limit display and a lower limit display alternatively selectable between displaying upper and lower flow limits or upper and lower pressure limits;
(b) a flow rate analog display for visibly displaying a measured volumetric flow rate only upon selection of said display of upper and lower flow rate limits; and
(c) a pressure analog display for visibly displaying a measured fluid pressure only upon selection of said upper and lower pressure limits.

26. A fluid delivery system as in claim 25 further comprising:
(a) a microprocessor operatively connected to said panel for automatically converting said upper and lower pressure limits to corresponding upper and lower flow rate limits based upon measured fluid pressure and measured volumetric flow rate; and
(b) a automatic mode switch operatively connected for selecting said upper and lower pressure limit display and for activating said microprocessor to convert said upper and lower pressure limits to upper and lower flow rate limits based upon a measured volumetric flow rate and a measured fluid pressure measured when said automatic mode switch is actuated.

27. A fluid delivery system as in claim 1 further comprising:
(a) an upper pressure limit display; and
(b) a lower pressure limit display.

28. A fluid delivery system as in claim 27 further comprising an analog display, positioned on said panel and interposed between said upper pressure limit display and said lower pressure limit display, for visually depicting a measured fluid pressure in said fluid flow path relative to said upper limit and said lower limit for said pressure.

29. A fluid delivery system as in claim 1 further comprising:
(a) communication means operatively connected between said two or more visible displays and said associated control mechanism, wherein at least one of said plurality of control elements is responsive to a set value displayed in at least one of said two or more visible displays to obtain in said blood mixture fluid delivery system an operational value for said at least one of said plurality of controllable characteristic, such operational value being a physical equivalence to said displayed set value; and
(b) adjustment means, operatively connected to said at least one visible display, for adjusting said set value.

30. A fluid delivery system as in claim 29 wherein said adjustment means comprises:
(a) an adjustment mode switch positioned on said panel adjacent to said at least one visible display, said switch manually operable to select an adjustment mode of operation; and
(b) a set knob, positioned on said panel and operatively connected to said associated control mechanism upon manually selecting said adjustment mode of operation, for setting said set value of said at least one of said plurality of controllable characteristics.

31. A fluid delivery system as in claim 30 wherein;
(a) said blood mixture fluid is a cardioplegia fluid;
(b) said at least one visible display comprises a blood:crystalloid ratio display, wherein said blood:crystalloid ratio display indicates a set value for said ratio of blood to crystalloid in said cardioplegia fluid; and
(c) said adjustment mode switch is positioned on said panel adjacent to said blood:crystalloid ratio display, said adjustment mode, when active, allowing the adjustment of said set value via said set knob, wherein upon adjustment at least one of said plurality of control elements are actuated to adjust said ratio of blood to crystalloid in said cardioplegia fluid to obtain a corresponding operational value in said fluid flow path.

32. A fluid delivery system as in claim 30 wherein:
(a) said blood mixture fluid is a cardioplegia fluid;

(b) said at least one visible display comprises an arresting agent display, wherein said arresting agent display indicates a set value for a quantity of arresting agent in said cardioplegia fluid; and (c) said adjustment mode switch is positioned on said panel adjacent to said arresting agent display, said adjustment mode, when active, allowing the adjustment of said set value via said set knob, wherein upon adjustment at least one of said plurality of control elements are actuated to adjust said quantity of arresting agent in said cardioplegia fluid to obtain a corresponding operational value in said fluid flow path.

33. A fluid delivery system as in claim 30 wherein:

(a) said at least one visible display comprises a fluid temperature display, wherein said fluid temperature display indicates a set value for a temperature in said blood mixture fluid; and (b) said adjustment mode switch is positioned on said panel adjacent to a said fluid temperature display, said adjustment mode, when active, allowing the adjustment of said set value via said set knob, wherein upon adjustment at least one of said plurality of control elements are actuated to adjust said temperature in said blood mixture fluid to obtain a corresponding operational value in said fluid flow path.

34. A fluid delivery system as in claim 30 wherein:

(a) said at least one visible display with which said adjustment mode switch is associated comprises a digital display having at least two levels of light intensity; and (b) said digital display is activated from a low level of light intensity to a high level of light intensity upon selection of said adjustment mode.

35. A fluid delivery system as in claim 1 wherein said two or more visible displays, each representing at least one of said plurality of controllable characteristics of said blood mixture fluid delivery system, comprise:

(a) a first display of a controllable characteristic of primary significance and a second display of a controllable characteristic of secondary significance; and (b) wherein said first display of said controllable characteristic of primary significance is constructed on said display panel with greater visibility than said second display of a controllable characteristic of secondary significance.

36. A fluid delivery system as in claim 35 wherein said construction by which said first display has greater visibility than said second display comprises said first display being larger than said second display, said primary significance of said first display being determined by said plurality of controllable characteristic and which of such plurality is critical to the delivery of said blood mixture fluid.

37. A fluid delivery system as in claim 35 wherein said construction by which said first display has greater visibility than said second display comprises said first display being brighter than said second display, said primary significance of said first display being determined by said plurality of controllable characteristic and which of such plurality is critical to the delivery of said blood mixture fluid.

38. A fluid delivery system as in claim 35 wherein said construction by which said first display has greater visibility than said second display comprises said first display having a first color of primary prominence and said second display having a second color of secondary prominence, said primary significance of said first display being determined by said plurality of controllable characteristic and which of such plurality is critical to the delivery of said blood mixture fluid.

39. A fluid delivery system as in claim 35 wherein said construction by which said first display has greater visibility than said second display comprises said first display which has a first color red of primary prominence and said second display has a second color green of secondary prominence.

40. A fluid delivery system as in claim 35 wherein said construction by which said first display of said characteristic of primary significance has greater visibility than said second display of said characteristic of secondary significance comprises positioning said first display of said primarily significant characteristic along a vertical center line of said display panel and positioning said second display of said characteristic of secondary significance adjacent to said vertical center line of said display panel, said primary significance being attributable to the criticality of said characteristic of primary significance to the delivery of said blood mixture fluid.

41. A fluid delivery system as in claim 1 further comprising:

(a) an information screen positioned adjacent to and viewable simultaneously with said visible schematic representation of said fluid flow path, said information screen visibly presenting a plurality of selectable informational messages regarding said blood mixture fluid delivery system; and (b) means for selecting one or more of said plurality of informational messages to be visibly presented.

42. A fluid delivery system as in claim 41 wherein said means for selecting said one or more of said plurality of informational messages to be visibly presented on said information screen comprises:

(a) a plurality of independently activatable function keys by which a function of the blood mixture fluid delivery system can be selected, corresponding to an activated function key, thereby determining the informational messages to be displayed; and (b) automatic circuitry connected to said panel, said information screen and said function keys for causing informational messages to be displayed regarding said plurality of controllable characteristics of said blood mixture fluid system and which of said plurality of function key is selectably activated.

43. A fluid delivery system as in claim 41 wherein said means for selecting said informational messages to be presented further comprises a plurality of variable function keys, a function of one or more of said variable function keys being indicated in one or more of a plurality of display fields within said information screen.

44. A fluid delivery system with an information screen as in claim 41 further comprising:

(a) a plurality of information presentation fields, each at a predetermined position on said information screen;

(b) a plurality of manually actuatable variable function keys positioned adjacent various ones of said plurality of presentation fields;

(c) preprogrammed circuitry by which a current function of each of said variable function keys is determined so that activation of a selected one of said keys adjacent a particular information field generates another visible presentation, so that said presentation is thereby selected.

45. A fluid delivery system as in claim 41 further comprising:

(a) a plurality of message fields at predetermined separate locations on the face of said information screen;

(b) a plurality of variable function keys positioned around a border of said information screen at predetermined locations adjacent to said predetermined locations of said message fields; and (c) input/output circuitry by which said message fields display preprogrammed queries to which an operator may respond with one or another query responses through actuation of one or another of said variable function keys, which one or other variable function key is positioned adjacent to a corresponding message field in which said query responses are displayed.

46. A fluid delivery system as in claim 41 wherein:

(a) said means for selecting said informational message to be displayed on said information screen further comprises switches positioned on said display panel actuatable to select a designated mode of operation from a predetermined set of modes of operation, including a set-up mode, a system priming mode, a system running mode, a volume delivered and dose mode, a default value setting mode, and a timer mode; and (b) automatic control means responsive to each of said selective actuation of said mode selection switches for automatically displaying preprogrammed messages corresponding to system characteristics appropriate for display in each of said selected modes of operation.

47. A fluid delivery system as in claim 41 wherein said means for selecting said message to be displayed further comprises a switch actuatable to initiate a priming sequence, said priming sequence requiring said associated control mechanism to ready said fluid delivery system for blood mixture fluid delivery by moving said blood mixture fluid into said delivery system from said at least one source and placing said plurality of control elements in a ready condition.

48. A cardioplegia delivery system having a display panel, which said cardioplegia fluid delivery system has mechanisms for infusing blood, crystalloid, heart arresting agent and for controlling a plurality of controllable characteristics along a fluid flow path defined by said fluid delivery system, said display panel of said cardioplegia fluid delivery system comprising:

(a) a digital display of numeric values that display a settable upper limit and a settable lower limit for a specified controllable characteristic; and (b) an analog display depicting an actual value of said specified controllable characteristic measured along said fluid flow path, for which said upper and lower limits are represented and provide a basis of relative measurement for said actual value, wherein such combination of digital and analog displays empowers a user to immediately assess potentially critical conditions relating to infusion of cardioplegia fluid.

49. A fluid delivery system as in claim 48 wherein:

(a) said upper limit digital display is positioned on said panel vertically above and spaced apart a predetermined linear distance from said lower limit digital display; and (b) said analog display is positioned between said lower and upper limit digital displays and comprises a visual depiction of a variable length line extending from said lower limit partially toward said upper limit along said linear distance therebetween, said variable length line being representative of said measured actual value relative to said settable upper and lower limits.

50. A fluid delivery system as in claim 49 wherein said visible depiction of said variable length line comprises a series of LED indicators aligned along said linear distance between said upper and said lower limit digital displays, which LED indicators are sequentially lighted to produce a depiction of a line corresponding to a proportional length signifying the actual value relative to the settable upper and lower limits.

51. A fluid delivery system as in claim 49 wherein said specified controllable characteristic is a volumetric flow rate of said cardioplegia fluid along said fluid flow path, wherein said analog display depicts a measured volumetric flow rate relative to set upper and lower limits, such set upper and lower limits being respectively displayed in said upper limit digital display and said lower limit digital display.

52. A display panel as in claim 49 wherein said specified controllable characteristic is a cardioplegia fluid pressure substantially at a point of delivery to said patient, wherein said analog display depicts a measured pressure at said point of delivery relative to set upper and lower limits, such set upper and lower limits being respectively displayed in said upper limit digital display and said lower limit digital display.

53. A fluid delivery system as in claim 49 wherein said digital display of numeric values that display a settable upper limit and a settable lower limit for a specified controllable characteristic comprise a single display, said single display being selectably switchable between displaying an upper limit and a lower limit for said specified characteristic and displaying an upper limit and a lower limit for another characteristic, and said analog display comprises a first analog display for depicting a first measured actual value for said specified characteristic and a second analog display for depicting a second measured actual value for said other characteristic, which analog first and second displays are side by side, but which are activatable separately for displaying said specified or said other characteristic corresponding to the selected specified or other characteristic for which said upper and lower limits are displayed.

54. A fluid delivery system as in claim 53 wherein said first and second analog displays further comprise illuminated labels to identify the characteristic for which said upper and lower limits are associated and which of first or second measured actual values are being displayed in said respective analog display.

55. A fluid delivery system as in claim 53 wherein:

(a) said specified characteristic, for which upper and lower limits are selectably displayed and for which said first analog display is provided, corresponds to a cardioplegia fluid volumetric flow rate; and (b) said other characteristic, for which upper and lower limits are selectably displayed and for which said second analog display is provided, corresponds to a cardioplegia fluid delivery pressure measured at said patient.

56. A cardioplegia fluid delivery system having a display panel and controls for use by an operator to control delivery of a cardioplegia fluid, which system has mechanisms for infusing said cardioplegia solution into a patient's heart, said display panel and controls of said system comprising:

(a) a panel;

(b) a visible representation of alternative cardioplegia fluid delivery points in said patient's heart, positioned on said panel, such visible representation including a delivery point in said patient's aortic root for antegrade delivery and a delivery point in said patient's coronary sinus for retrograde delivery;

(c) control means in said cardioplegia fluid delivery system, by which said delivery point in the patient's heart may be alternative selected by said operator; and (d) indicia means, coupled to said control means and positioned on said panel adjacent to said visible representation, for indicating whether said delivery point of said cardioplegia fluid is consistent with said retrograde delivery or said antegrade delivery.

57. A cardioplegia fluid delivery system as in claim 56 wherein:

(a) said visible representation includes a visible schematic depiction of a heart, including a schematic depiction of an aortic root and/or a coronary ostia on one side of said schematic depiction of the heart and a schematic depiction of a coronary sinus on another side of the schematic depiction of the heart;

(b) a first flow path representation line, positioned on said panel, beginning at a point adjacent to said schematic depiction of the heart and terminating at a point in said schematic depiction of an aortic root and/or a coronary ostia and a second flow path representation line, positioned on said panel, beginning at a point adjacent to said schematic depiction of the heart and terminating at a point in said schematic depiction of a coronary sinus; and (c) wherein said indicia means comprises a first light positioned along said first flow path representation line, said first light indicating, when in an "on" state, that cardioplegia fluid is being delivered to said heart in an antegrade fashion and a second light positioned along said second flow path representation line, said second light indicating, when in an "on" state, that cardioplegia fluid is being delivered to said heart in a retrograde fashion.

58. A cardioplegia fluid delivery system as in claim 57 wherein said indicia means comprising said first and second lights further comprises a dynamic first set of lights and a dynamic second set of lights, such dynamic sets flash sequentially along said first and second path representation lines to visually depict movement of cardioplegia fluid toward the aortic root and/or coronary ostia or, alternatively, movement of cardioplegia fluid toward the coronary sinus according to said selection of antegrade delivery or retrograde delivery, respectively.

59. A cardioplegia fluid delivery system as in claim 57 wherein, (a) said control means includes a selection valve mechanism and a selector means;

(b) said first flow path representation line corresponds to an antegrade cardioplegia feed line coupled to an antegrade catheter positioned within the aortic root of said patient's heart, said antegrade feed line being operatively coupled to and selectable by said selection valve mechanism;

(c) said second flow path representation line corresponds to a retrograde cardioplegia feed line coupled to a retrograde catheter positioned within the coronary sinus of said patient's heart, said retrograde feed line being operatively coupled to and selectable by said selection valve mechanism; and (d) said selector means, positioned on said panel, permits said operator to select antegrade delivery or retrograde delivery to said patient's heart, such selected delivery being (i) visibly indicated to said operator along said first or second flow path representation lines, and (ii) established by said selection valve mechanism to direct flow of said cardioplegia fluid through said selected cardioplegia feed line to such line's respective catheter.

60. A cardioplegia fluid delivery system as in claim 59 further comprising:

(a) a valve position sensor at said selection valve mechanism for producing a signal representative of a position of said selection valve mechanism;

(b) a sensory input signal communicating between said valve position sensor and said selector means for automatically signaling said indicia means to display between said antegrade or said retrograde delivery corresponding to said position of said selection valve mechanism.

61. A cardioplegia fluid delivery system means as in claim 60 further comprising:

(a) a controllable valve positioning device connected to said selection valve mechanism;

(b) said sensory signal connector capable of providing control signals from said selector means to said controllable valve positioning device; and (c) said selector means capable of generating control signals receivable by said valve positioning means for positioning said selection valve according to said selected delivery point.

* * * * *

UNITED STATES PATENT AND TRADEMARK OFFICE
CERTIFICATE OF CORRECTION

PATENT NO. : 5,573,502
DATED : November 12, 1996
INVENTOR(S) : Andrew D. LeCocq, et al.

It is certified that error appears in the above-indentified patent and that said Letters Patent is hereby corrected as shown below:

Column 9, Line 30 --
        Replace:     "5/6"
        With:     -- 5/16 --

Column 14, Line 64 --
        Replace:     "deliver"
        With:     -- delivery --

Column 19, Line 7 --
        Replace:     "units+by"
        With:     -- units / by --

Column 19, Lines 61 & 66 --
        Replace:     "258"
        With:     -- 238 --

Signed and Sealed this

Eighth Day of April, 1997

Attest:

BRUCE LEHMAN

*Attesting Officer*      *Commissioner of Patents and Trademarks*